United States Patent
Dudkin et al.

(10) Patent No.: US 12,084,475 B2
(45) Date of Patent: Sep. 10, 2024

(54) METHODS FOR SITE SPECIFIC CONJUGATION OF PROTEINS CONTAINING GLYCOSYLATED Fc DOMAINS

(71) Applicant: Janssen Biotech, Inc., Horsham, PA (US)

(72) Inventors: Vadim Dudkin, Chalfont, PA (US); Shalom Goldberg, Merion Station, PA (US); Michael J. McCauley, Abington, PA (US); Kristen Wiley, Trappe, PA (US)

(73) Assignee: Janssen Biotech, Inc., Horsham, PA (US)

(*) Notice: Subject to any disclaimer, the term of this patent is extended or adjusted under 35 U.S.C. 154(b) by 418 days.

(21) Appl. No.: 17/324,150

(22) Filed: May 19, 2021

(65) Prior Publication Data

US 2021/0363177 A1 Nov. 25, 2021

Related U.S. Application Data

(60) Provisional application No. 63/027,400, filed on May 20, 2020.

(51) Int. Cl.
| | |
|---|---|
| *C07K 1/107* | (2006.01) |
| *A61K 47/54* | (2017.01) |
| *A61K 47/62* | (2017.01) |
| *A61K 47/68* | (2017.01) |

(52) U.S. Cl.
CPC .......... *C07K 1/1077* (2013.01); *A61K 47/549* (2017.08); *A61K 47/62* (2017.08); *A61K 47/68* (2017.08); *C07K 2317/41* (2013.01); *C07K 2319/30* (2013.01); *C07K 2319/91* (2013.01)

(58) Field of Classification Search
None
See application file for complete search history.

(56) References Cited

U.S. PATENT DOCUMENTS

| | | | |
|---|---|---|---|
| 11,629,122 B2 * | 4/2023 | Tsuchikama | C07D 403/12 424/179.1 |
| 2013/0266512 A1 | 10/2013 | Fox et al. | |
| 2017/0106096 A1 * | 4/2017 | Hu | C07K 16/30 |
| 2018/0044711 A1 * | 2/2018 | Spidel | C07K 16/00 |
| 2020/0024360 A1 | 1/2020 | Anderson et al. | |

FOREIGN PATENT DOCUMENTS

| | | | | |
|---|---|---|---|---|
| WO | WO 2015073746 A2 | 5/2015 | | |
| WO | WO 2015/191883 A1 | 12/2015 | | |
| WO | WO-2018218004 A1 * | 11/2018 | | A61K 31/40 |
| WO | WO 2019/057772 A1 | 3/2019 | | |
| WO | WO 2019125982 A1 | 6/2019 | | |
| WO | WO 2019224718 A2 | 11/2019 | | |

OTHER PUBLICATIONS

Strop et al., Chemistry and Biology 20: 161-167 (Year: 2013).*
Yamazoe et al., Bioconjugate Chemistry 33: 576-585 (Year: 2022).*
International Search Report issued in corresponding PCT Patent Application No. PCT/IB2021/054310, filed on May 19, 2021. Mailing Date of International Search Report: Sep. 27, 2021.
Written Opinion issued in corresponding PCT Patent Application No. PCT/IB2021/054310, filed on May 19, 2021. Mailing Date of Written Opinion: Sep. 27, 2021.
International Search Report issued in related PCT Patent Application No. PCT/IB2021/054308, filed on May 19, 2021. Mailing Date of International Search Report: Dec. 10, 2021.
Written Opinion issued in related PCT Patent Application No. PCT/IB2021/054308, filed on May 19, 2021. Mailing Date of Written Opinion: Dec. 10, 2021.
Schneider et al., "recent progress in transglutaminase-mediated assemblyof antibody-drug conjugates.", Analytical Biochemistry, Feb. 5, 2020, pp. 1-13, vol. 595.
Chandler et al., "Multi-isotype Glycoproteomic Characterization of Serun Antibody Heav Chains Reveals Isotype-and Subclass-Specific N-Glycosylation Profiles.", Molecular & Cellular Proteomics, Apr. 2019, pp. 686-703, vol. 18(4).
Dennler et al., "Enzymatic Antibody Modification by Bacterial Transgl utaminase", Antibody-Drug Conjugates, Methods in Molecular Biology, Jan. 1, 2013, pp. 205-215, vol. 1045, XP009178016.
Agarwal and Bertozzi, "Site-Specific Antibody—Drug Conjugates: The Nexus of Bioorthogonal Chemistry, Protein Engineering, and Drug Development.", Bioconjug Chem, 2015, pp. 176-192, vol. 26(2).
Ahmed et al., "Structural Characterization of Anti-Inflammatory Immunoglobulin G Fc Proteins.", J Mol Biol, 2014, pp. 3166-3179, vol. 426(18).
Bethea et al., "Mechanisms of self-association of a human monoclonal antibody CNTO607.", Prot Eng Des Sel, 2012, pp. 531-537, vol. 25(10).
Chothia & Lesk, "Canonical Structures for the Hypervariable Regions of Immunoglobins." J. Mol. Biol., 1987, pp. 901-907, vol. 196.
Chothia et al., "Conformations of Immunoglobulin hypervariable regions.", Nature, 1989, pp. 878-883, vol. 342.
Dall'Acqua et al., "Properties of Human IgG1s Engineered for Enhanced Binding to the Neonatal Fc Receptor (FcRn)*.", J Biol Chem, Aug. 18, 2006, pp. 23514-23524, vol. 281(33).
Dennler et al., "Microbial Transglutaminase and c-myc-Tag: A Strong Couple for the Functionalization of Antibody-Like Protein Scaffolds from Discovery Platforms.", Chembiochem, 2015, pp. 861-867, vol. 16(5).

(Continued)

*Primary Examiner* — Phuong Huynh
(74) *Attorney, Agent, or Firm* — Ice Miller LLP

(57) ABSTRACT

Provided herein are methods for site-specific conjugation of glycan intact antibodies by a transglutaminase. According to particular embodiments, the reaction conditions are maintained or reduced to a low-ionic strength condition, which allows for efficient and fast conjugation without the need for antibody deglycosylation. Also described are pharmaceutical compositions and uses related to the conjugation method.

17 Claims, 8 Drawing Sheets

Specification includes a Sequence Listing.

(56) References Cited

OTHER PUBLICATIONS

Houde D. et al., "Characterization of IgG1 Conformation and Conformational Dynamics by Hydrogen/Deuterium Exchange Mass Spectrometry.", Anal Chem., 2009, pp. 2644-2651, vol. 81(7).
Jeger et al., "Site-Specific and Stoichiometric Modification of Antibodies by Bacterial Transglutaminase**.", Angewandte Chemie, 2010, pp. 9995-9997, vol. 49(51).
Kabat and Wu, "Identical V Region Amino Acid Sequences and Segments of Sequences in Antibodies of Different Specificities. Relative Contributions of VH and VL Genes, Minigenesm and Complimentary Determining Regions to Binding of Antibody-Combining Sites.", J Immunol, Sep. 1991, pp. 1709-1719, vol. 147(5).
Kolb, et al., "Click Chemistry: Diverse Chemical Function from a Few Good Reactions.", Angew Chem Int Ed Engl., Jun. 1, 2001, pp. 2004-2021, vol. 40(11).
Liu et al., "High-throughput screening for developability during early-stage antibody discovery using selfinteraction nanoparticle spectroscopy.", mAbs, Mar./Apr. 2014, pp. 483-492, vol. 6(2).
Mackness et al., "Antibody Fc engineering for enhanced neonatal Fc receptor binding and prolonged circulation half-life.", mAbs, 2019, pp. 1276-1288, vol. 11(7).
Majumdar et al., "Correlations between changes in conformational dynamics and physical stability in a mutant IgG1 mAb engineered for extended serum half-life.", Mabs, 2015, pp. 84-95, vol. 7(1).
Mero et al., "A new method to increase selectivity of transglutaminase mediated PEGylation of salmon calcitonin and human growth hormone.", J Control Release, 2011, pp. 27-34, vol. 154(1).
Nahta and Esteva, "Trastuzumab: triumphs and tribulations.", Oncogene, 2007, pp. 3637-3643, vol. 26(25).
Sato, H., "E nzymatic procedure for site-specific pegylation of proteins.", Advanced drug delivery reviews, 2002, pp. 487-504, vol. 54(4).
Savoca et al., "Biocatalysis by Transglutaminases: A Review of Biotechnological Applications.", Micromachines, 2018, pp. 1-23, vol. 9(562), Basel.
Spicer and Davis, "Selective chemical protein modification.", Nature Communications, 2014, pp. 1-14, 5:4740.
Spolaore et al., "Local Unfolding Is Required for the Site-Specific Protein Modification by Transglutaminase.", Biochemistry, 2012, pp. 8679-8689, vol. 51.
Spolaore et al., "Site-Specific Transglutaminase-Mediated Conjugation of Interferon α-2b at Glutamine or Lysine Residues.", Bioconjugate chemistry, 2016, pp. 3695-3706, vol. 27(11).
Strop et al., "Location Matters: Site of Conjugation Modulates Stability and Pharmacokinetics of Antibody Drug Conjugates.", Chem Biol, Feb. 21, 2013, pp. 161-167, vol. 20(2).
Sugimura et al., "Identification of preferred substrate sequences of microbial transglutaminase from Streptomyces mobaraensis using a phage-displayed peptide library.", Arch Biochem Biophys, 2008, pp. 379-383, vol. 477(2).
Wada et al., "Influence of N-glycosylation on effector functions and thermal stability of glycoengineered IgG1 monoclonal antibody with homogeneous glycoforms.", Mabs, 2019, pp. 350-371, vol. 11(2).

* cited by examiner

SEQUENCE LISTING

<160> NUMBER OF SEQ ID NOS: 4

<210> SEQ ID NO 1
<211> LENGTH: 214
<212> TYPE: PRT
<213> ORGANISM: Homo sapiens

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                        85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 450
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

-continued

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 214
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

-continued

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 451
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Asp
            20                  25                  30

Ala Met His Trp Val Arg Gln Ala Pro Gly Lys Gly Leu Glu Trp Val
        35                  40                  45

Ser Glu Ile Ser Gly Ser Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Tyr Asp Ser Ser Leu Tyr Val Gly Asp Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly

-continued

```
305                 310                 315                 320
Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Leu Gly Lys
    450
```

METHODS FOR SITE SPECIFIC CONJUGATION OF PROTEINS CONTAINING GLYCOSYLATED Fc DOMAINS

CROSS-REFERENCE TO RELATED APPLICATIONS

This application claims the benefit of priority of U.S. Provisional Application No. 63/027,400, filed May 20, 2020, which is incorporated by reference herein, in its entirety and for all purposes.

SEQUENCE LISTING

The instant application contains a Sequence Listing which has been submitted electronically in ASCII format and is hereby incorporated by reference in its entirety. The ASCII copy, created on Apr. 27, 2021, is named JBI6303USNP1_SL.txt and is 12,288 bytes in size.

FIELD OF THE INVENTION

The invention relates to methods for site-specific conjugation of glycan intact antibodies by a transglutaminase under optimized buffer conditions for the generation of optimized antibody-drug-conjugates (ADCs) with better manufacturing and in vivo properties.

BACKGROUND OF THE INVENTION

Covalent attachment of molecules to a particular site on a large protein, such as a monoclonal antibody (mAb), is a technology that is increasing in importance. Therapeutic platforms that make use of site-specific conjugation, such as antibody-drug conjugates, are entering clinical development in growing numbers. As a result, novel methods to complement or replace existing approaches are of great value.

One approach to site-specific conjugation that has been described utilizes transglutaminase (TGase) enzymes. Transglutaminases are a large class of enzymes with representatives in microbes as well as higher organisms (Savoca et al., Micromachines (2018) 9(11): 562). These enzymes catalyze covalent bond formation between the ε-amino group of lysine and the γ-carboxamide group of glutamine sidechain of proteins resulting in an isopeptide bond. TGases play a role in multiple biological processes including blood coagulation, extracellular matrix assembly, and spore formation. In addition to their native function, some TGases can use other amides or amines in place of the glutamine or lysine sidechain, respectively, and thereby catalyze the covalent conjugation of small molecule substrates to proteins. For example, they can conjugate the primary amine of a drug to the side chain carboxyamide group of a glutamine residue of a protein or peptide and form an isopeptide bond between the drug and the protein or peptide.

The microbial TGase (MTG) from *S. mobarensis* has proven to be particularly useful for covalent conjugation of small molecules to protein sidechains. MTG was shown to catalyze the addition of PEG to a variety of proteins including recombinant human IL2 (Sato, Advanced drug delivery reviews (2002), 54(4):487-504), interferon (Spolaore et al., *Bioconjugate chemistry* (2016), 27(11): 2695-2706), and human growth hormone (Mero et al., *J Control Release* (2011), 154(1): 27-34) by using an amine-modified PEG for conjugation with the glutamine sidechains of proteins, or by using PEG modified with a Gln-containing dipeptide for conjugation to lysine sidechains of proteins. In each case, PEG was added selectively to just one or a small subset of Gln or Lys sidechains. While the substrate specificity of the *S. mobaraensis* microbial TGase (MTG) is not well understood, different studies have shown some degree of sequence selectivity for glutamine substrate (Sugimura et al., *Arch Biochem Biophys* (2008), 477(2):379-383) as well as some degree of dependence on secondary structure (Spolaore et al., Biochemistry (2012), 51(43): 8679-8689). Currently, empirical approaches are typically used to determine if MTG can be used for selective conjugation of a particular protein.

MTG has been used to selectively conjugate small molecules to monoclonal antibodies at specific sites. Two different approaches have been demonstrated for conjugation of amine-containing payloads to Gln sidechains on mAbs, one using a tagging approach and the second making use of a serendipitous discovery that a particular Gln residue can be a good MTG substrate under certain conditions. A tag-based approach has also been described for conjugation of Gln-containing payloads to a lysine sidechain.

Jeger et al., in the course of preparing radioimmunoconjugates, demonstrated that the rate of modification of mAbs with MTG is much faster with deglycosylated antibodies than if the N-linked glycans at Asn297 are intact (Jeger et al., *Angewandte Chemie* (2010), 49(51): 9995-9997) and that the modification was highly specific to one particular Gln site on the mAb. The conjugation site was determined to be Gln295, a position in the CH2 domain that is conserved across all human IgG isotypes and is two residues upstream from the glycosylation site. Deglycosylation followed by MTG-catalyzed conjugation to Gln295 has since become the traditional approach for preparing antibody-radioconjugates, antibody-drug conjugates, and other molecules. While the MTG driven conjugation method does not require antibody engineering, the conjugation of this approach requires removal of the glycan at Asn297. The removal of the glycan at Asn297 has been shown to impact the immunological properties of the antibody, as binding to Fc receptors is abrogated, and has been shown to impact the biophysical properties of the antibody, as reduction in thermal stability has been observed, with a decrease in melting temperature of the CH2 domain of up to 7-8° C. after glycan removal.

A tag-based method for site-selective mAb conjugation with transglutaminase has also been demonstrated. Appending or inserting a "Q-tag"—a short Gln-containing peptide such as LLQG—at certain positions in the mAb was shown to allow selective conjugation at the tag without the need for deglycosylation (Strop et al., *Chem Biol* (2013), 20(2):161-167). A preferred approach has been to introduce the Q-tag at the C-termini of the mAb light and heavy chains through the addition of an exogeneous peptide sequence. A similar approach has been described using the c-myc tag (Dennler et al., *Chembiochem* (2015), 16(5):861-867).

Site-specific conjugation has become a key area of focus in the antibody-drug conjugate (ADC) field (Agarwal, P. and C. R. Bertozzi, *Bioconjug Chem*, (2015), 26(2): 176-92), as it has been demonstrated that both efficacy and safety of ADCs can be increased with site-specific methods as compared to random conjugation.

However, efficient methods of site-specific conjugation of antibodies that will preserve the immunological and biophysical properties of the conjugated antibody, e.g., that will preserve the N-linked glycans and that do not introduce Gln-containing peptide tags, are still needed to generate safe and efficacious ADCs.

BRIEF SUMMARY OF THE INVENTION

Provided herein are methods for site specific conjugation of antibodies without the need for antibody deglycosylation. In certain embodiments, the invention provides a method of producing a conjugated antibody comprising reacting a glycosylated or glycan intact antibody or Fc fusion protein with an amine compound in the presence of transglutaminase in low-ionic strength conditions.

In one aspect, provided herein are methods for conjugation of glycosylated antibodies. An embodiment of the method comprises the step of contacting a glycan intact antibody with a primary amine compound in the presence of transglutaminase under low-ionic strength conditions that allow for a reaction of the primary amine with the antibody despite the presence of glycans. In certain embodiments, the antibody is glycosylated. In certain embodiments the antibody is glycosylated at Asn297. The present disclosure is based on the discovery that low-ionic strength buffer conditions allow for conjugation of glycosylated antibody and does not require the preliminary deglycosylation step required in traditional conjugation methods.

Embodiments of the method further comprise reducing the ionic strength of the transglutaminase preparation and/or the antibody preparation prior to reacting with the amine compound to provide a low-ionic strength transglutaminase preparation and/or antibody preparation. This additional step is preferred when the antibody and/or microbial transglutaminase preparation is provided in a high ionic strength buffer or contains unwanted additives that will affect the rate of the transglutamination reaction.

In certain embodiments, the low-ionic strength condition comprises 10 mM or less of sodium phosphate, potassium phosphate, sodium acetate, or Tris buffer. In another aspect, the degree of labeling (DOL) of the conjugated antibody obtained is at least 1.8. In some embodiment, the DOL is 2.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIG. 2B shows an enlarged version of the LC trace from 25-35 minutes, highlighting the peaks containing the Gln295 amino acid in the azide-conjugated antibody.

DETAILED DESCRIPTION OF THE INVENTION

Figure 1:
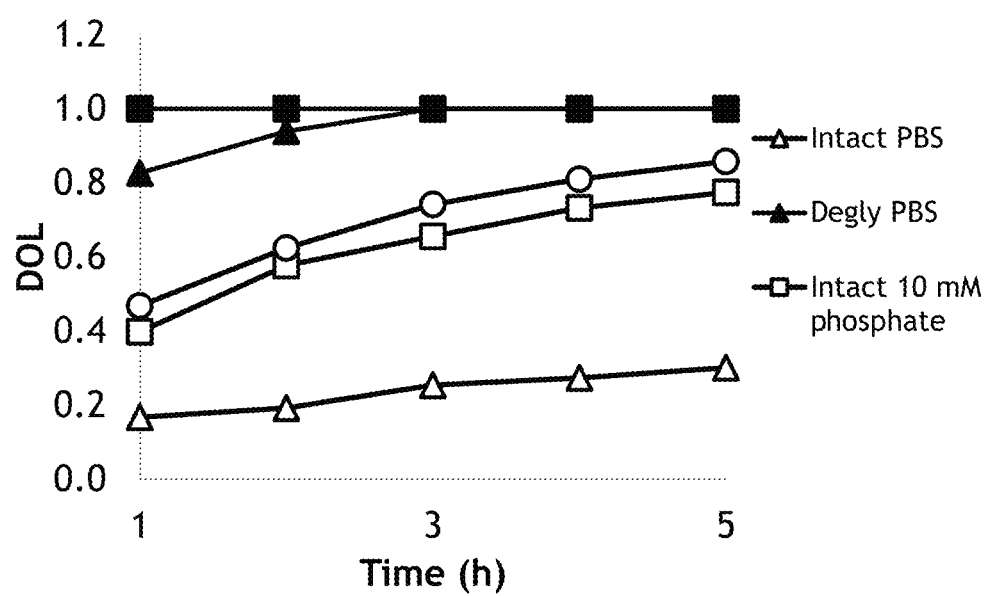
FIG. 1 shows the rate of MTG-catalyzed conjugation of 3-APA to intact and deglycosylated trastuzumab in different reaction buffer compositions. The degree of labeling (DOL) per heavy chain is shown as a function of time.
Figure 2A:
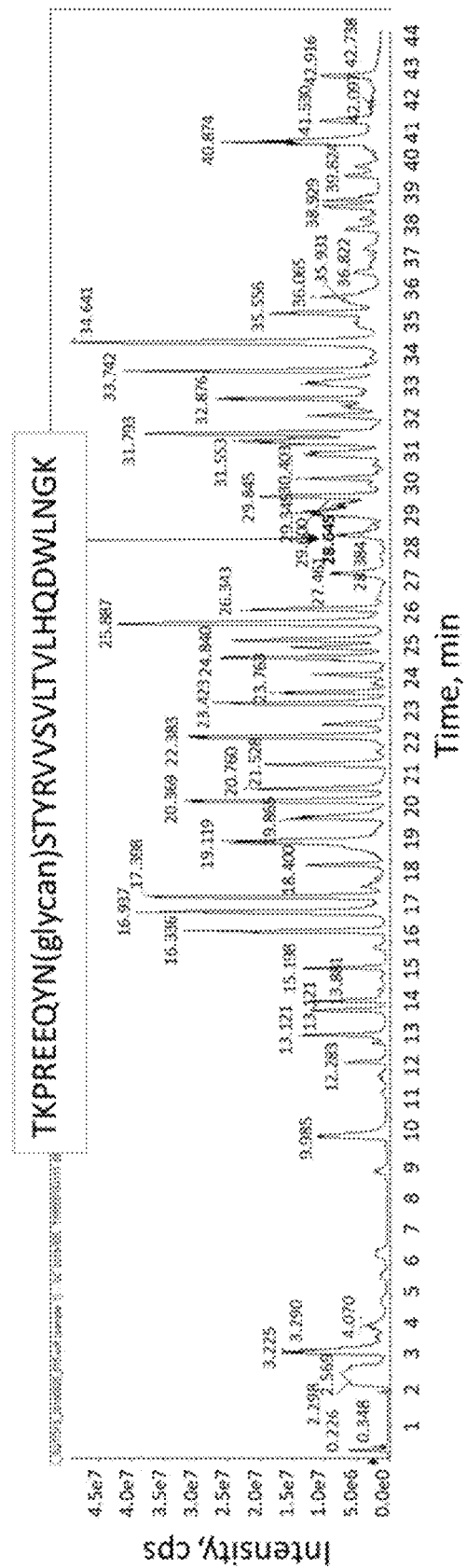
FIG. 2A shows the peptide mapping of glycan-intact trastuzumab. Trastuzumab was digested with trypsin and peptides were analysed by LC-MS. The peak corresponding to the HC peptide 289-317 containing the Gln295 glycosylation Gln295 shows a retention time of 28.65 min
Figure 2B:
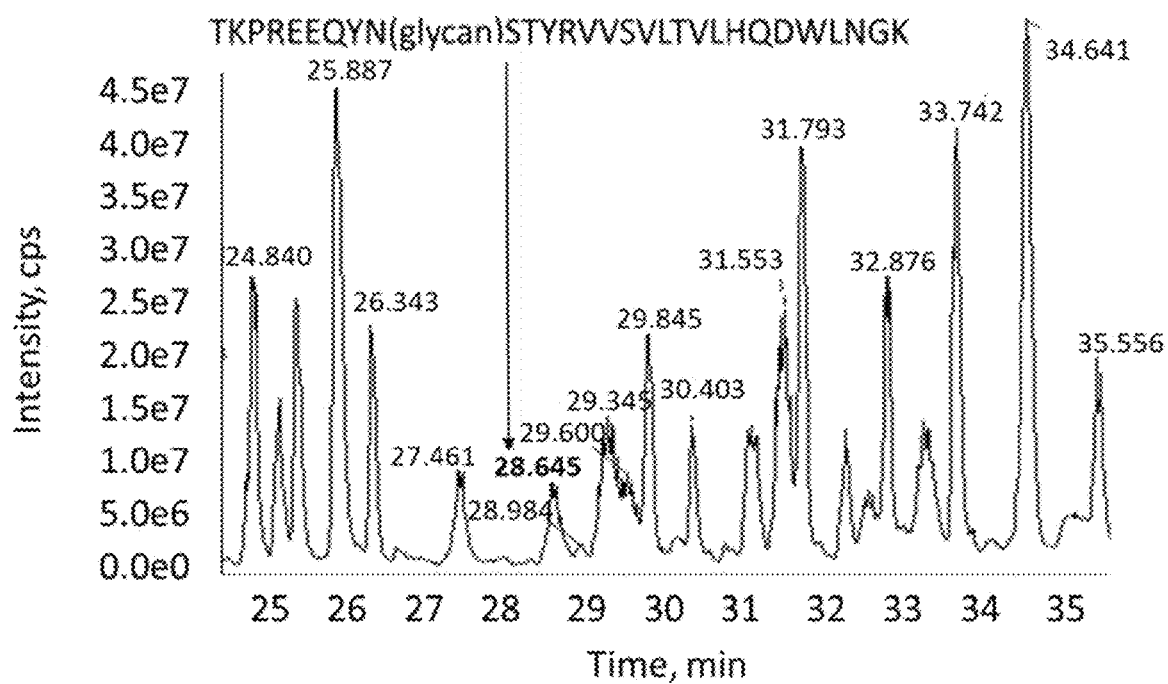
FIG. 2B shows an enlarged version of the LC trace from 25-35 minutes, highlighting the peaks containing the Gln295 amino acid in the intact mAb.
Figure 2C:
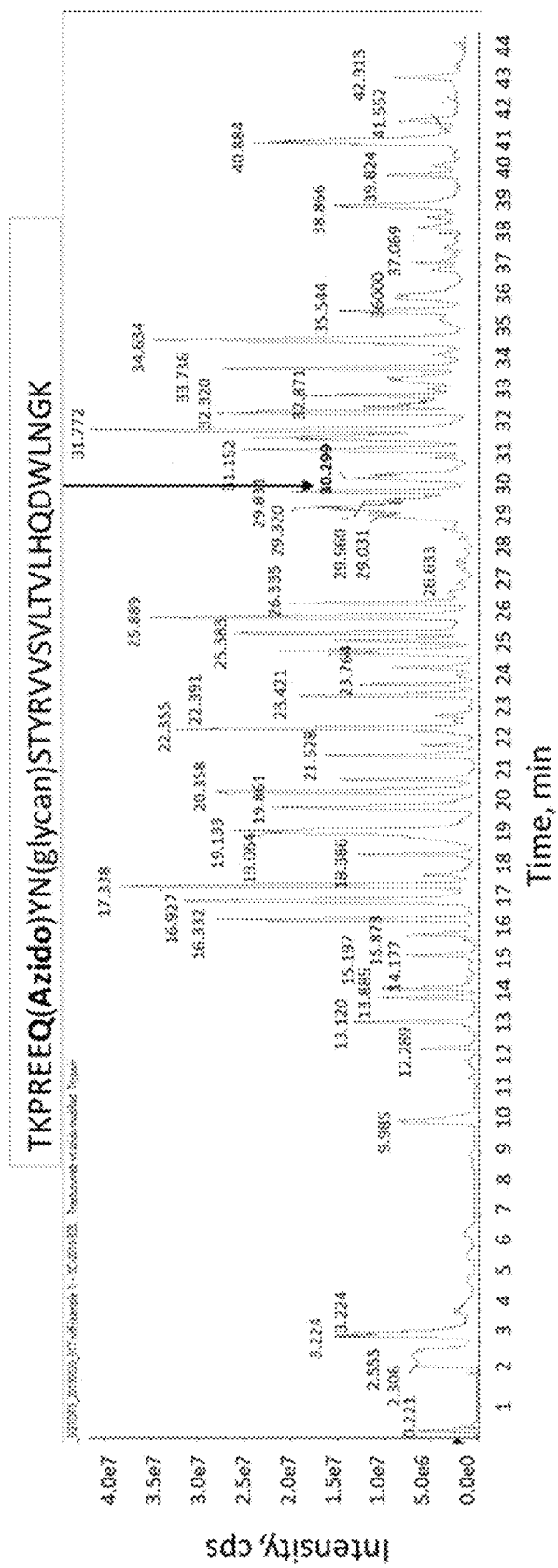
FIG. 2C shows the peptide mapping of glycan-intact trastuzumab modified with 3-APA. Site of 3-APA addition was determined by trypsin digestion followed by LC-MS analysis. The peak corresponding to the HC peptide 289-317 containing the site of glycosylation Gln295 (28.65 min retention time) observed in intact sample is absent in azide-conjugated sample and replaced with peptide corresponding to the HC 289-317 with a +83 Da modification at Gln295 position (30.3 min retention time).
Figure 2D:
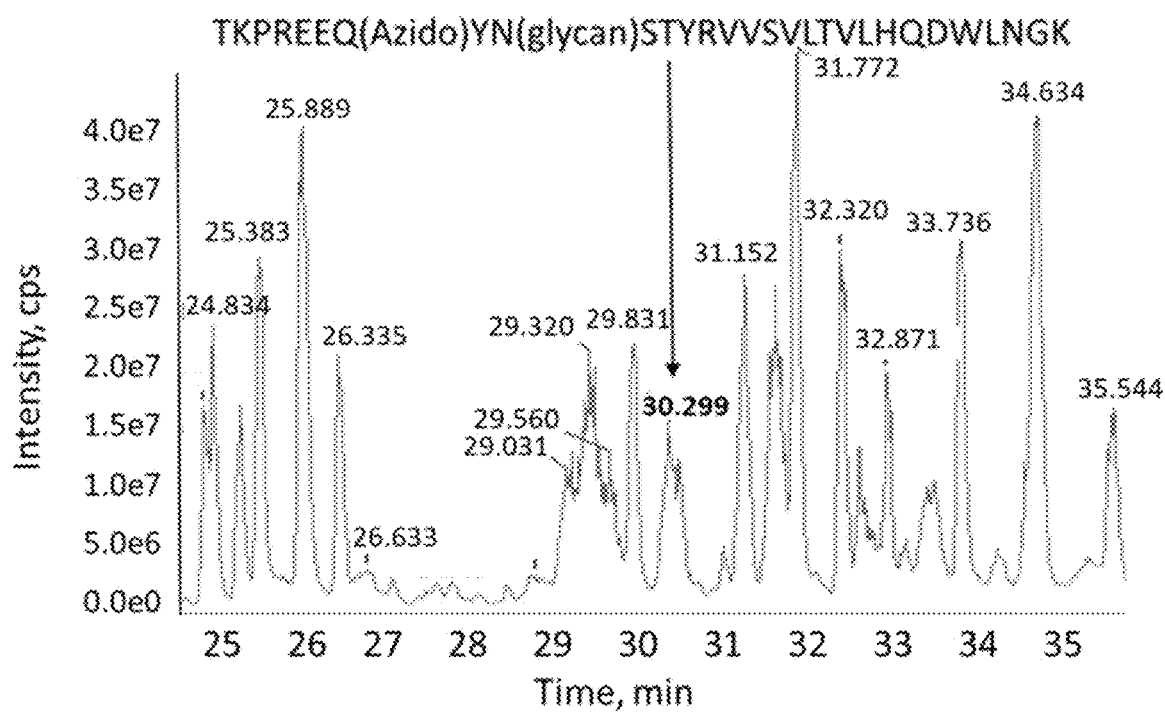

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

The numbering of amino acid residues of the antibody constant region throughout the specification is according to the EU index as described in Kabat et al., Sequences of Proteins of Immunological Interest, 5th Ed. Public Health Service, National Institutes of Health, Bethesda, MD (1991), unless otherwise explicitly stated.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

Terminology

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, exemplary materials and methods are described herein. In describing and claiming the present invention, the following terminology will be used.

It must be noted that as used herein and in the appended claims, the singular forms "a," "an," and "the" include plural reference unless the context clearly dictates otherwise. Thus, for example, reference to "a cell" includes a combination of two or more cells, and the like.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

"Antigen binding fragment" or "antigen binding domain" refers to a portion of the protein that binds an antigen. Antigen binding fragments may be synthetic, enzymatically obtainable or genetically engineered polypeptides and include portions of an immunoglobulin that bind an antigen, such as VH, the VL, the VH and the VL, Fab, Fab', F(ab')$_2$, Fd and Fv fragments, domain antibodies (dAb) consisting of one VH domain or one VL domain, shark variable IgNAR domains, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multispecific proteins comprising the antigen binding fragments. Antigen binding fragments (such as VH and VL) may be linked together via a synthetic linker to form various types of single antibody designs where the VH/VL domains may pair intramolecularly, or intermolecularly in those cases when the VH and VL domains are expressed by separate single chains, to form a monovalent antigen binding domain, such as single chain Fv (scFv) or diabody. Antigen binding fragments may also be conjugated to other antibodies, proteins, antigen binding fragments or alternative scaffolds which may be monospecific or multispecific to engineer bispecific and multispecific proteins. As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen than the parent antibody or a parent antibody fragment.

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "antibody" or "immunoglobulin" is used in a broad sense and includes immunoglobulin or antibody molecules including polyclonal antibodies, monoclonal antibodies including murine, human, human-adapted, humanized and chimeric monoclonal antibodies, and antigen-binding fragments thereof.

In general, antibodies are proteins or peptide chains that exhibit binding specificity to a specific antigen, referred to herein as a "target". Antibody structures are well known. An intact "antibody" comprises at least two heavy (H) chains and two light (L) chains inter-connected by disulfide bonds. See generally, Fundamental Immunology, Ch. 7 (Paul, W., ed., 2nd ed. Raven Press, N.Y. (1989)) (incorporated by reference in its entirety for all purposes). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains. Accordingly, the antibodies of the invention can contain a kappa or lambda light chain constant domain. According to particular embodiments, the antibodies of the invention include heavy and/or light chain constant regions from mouse antibodies or human antibodies. Each of the four IgG subclasses has different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. An antibody useful for the invention can have no or minimal effector function, but retain its ability to bind FcRn. "Full length antibodies" are comprised of two heavy chains (HC) and two light chains (LC) inter-connected by disulfide bonds as well as multimers thereof (e.g. IgM).

The term "Fc fusion protein" refers to a fusion protein comprising at least one Fc polypeptide linked to a protein or peptide of interest by a C- or N-terminal fusion, wherein the Fc polypeptide of the Fc fusion protein comprises an IgG CH2 and an IgG CH3 constant domain sequence.

As used herein, the term "engineered antibody" refers to an antibody, or a fragment thereof, comprising at least one engineered constant region, e.g., an engineered Fc region, an engineered Cκ region and/or an engineered Cλ region. The engineered antibody can comprise one or more mutations, one or more amino acid residue deletion or one or more amino acid insertion.

The term "glycan" refers to a polysaccharide, or oligosaccharide. Glycan is also used to refer to the carbohydrate portion of a glycoconjugate such as an antibody. O- and N-linked glycans are very common in eukaryotes. N-linked glycans are found attached to the R-group nitrogen (N) of asparagines in Asn-X-Ser or Asn-X-Thr sequences, where X is any amino acid.

The term "exo-glycosidase" or "exoglycosidase" refers to an enzyme capable of hydrolyzing a terminal glycosidic bond of a glycan structure. Example of suitable exo-glycosidase include, but are not limited to sialidase, galactosidase, alpha-fucosidase, alpha-manosidase. The term "endo-glycosidase" or "endoglycosidase" refers to an enzyme capable of hydrolyzing glycosidic bonds between residues that are not the terminal residues of glycan structures. Endo-glycosidase hydrolyze glycan bonds randomly from the inner sites of whole glycan. Examples include, but are not limited to endo-H, endo-F3, Endo-F2, and Endo-F1.

The term "deglycosylated antibody" refers to an antibody in which the glycan group at N297 was removed, thereby opening Q295 to conjugation with transglutaminase. The traditional conjugation methods known in the art, provide a method that encompasses this deglycosylation process to remove glycan at N297, prior to conjugation with transglutaminase. A "glycosylated antibody" or "glycosylated Fc fusion protein" refers to an antibody or Fc fusion protein, respectively, that has an N-linked glycan at position N297 and/or other residues.

As used herein, the term "antibody glycan" refers to the N-linked glycan at position Asn297 within the Fc region of monoclonal antibody heavy chains.

The term "glycan intact antibody" or "intact antibody" or "native antibody" refers to an antibody molecule that comprises an intact glycan content and whose glycan content is unchanged compared to the native antibody. A glycan intact antibody is an antibody whose glycans have not been hydrolyzed by endo or exo-glycosidases (such as, but not limited to PNGase F or endo F), or an antibody that has not been modified by glycan engineering (i.e., the antibody is not "glycan-engineered," such as by reducing the glycan or adding to the glycan either natural or unnatural sugars). In a glycan intact antibody, heterogenous N-linked glycans are attached to an Asparagine at position 297 (N297) in the CH2 domain of the Fc region of monoclonal antibody heavy chains.

The Fc region of IgG contains two glycans, one per heavy chain, attached to the single conserved glycosylation site at asparagine (Asn) 297. Each glycan can assume over 30 different forms, a diversity that affords the opportunity to fine-tune humoral immunity. There are 3 major classes of glycans—G0, G1, G2, according to the number of terminal galactoses 0, 1, or 2, respectively. Complex oligosaccharides comprising a core fucose in addition to the terminal galactose are described as G0F, G1F and G2F (e.g., G2F refers to two terminal galactoses and core fucose). Glycoforms lacking terminal galactose (termed G0, denoting zero galactoses) are particularly proinflammatory because they confer an enhanced ability to fix complement and to engage the activating IgG receptor FcγRIIIa while simultaneously blocking anti-inflammatory mechanisms mediated through sialylated and/or bigalactosylated (G2) glycans. Other small forms of glycans include G0F (no galactoses, no bisecting N-acetylglucosamine, with core fucose), and G1F (galactose attached to either the α1,6 or α1,3 arm).

The term "conjugated antibody" or "conjugate" refers to an antibody covalently linked to one or more chemical moieties; and the term "conjugated Fc fusion protein" refers to an Fc fusion protein covalently linked to one or more chemical moieties. The chemical moiety that is covalently linked to an antibody or Fc fusion protein can include a linker, a reactive linker, an amine linker, a payload, a reactive payload, an amine payload and/or a reactive-linker-payload.

As used herein, the term "antibody-payload conjugate", "reactive payload", "conjugate" or "antibody drug conjugate" or "ADC" refers to an antibody, or fragment thereof, that have been chemically linked to cytotoxic or cytosolic drug/agent, toxins or radionuclides referred to herein as a "payload" and that are capable of binding tumor-specific or tumor-associated cell surface antigens. Typically, antibody drug conjugates (ADC) are formed by covalently linking anticancer drugs to mAbs through a stable linker system. For example, tumor cell killing may occur upon binding of the drug conjugate to a tumor cell and release or/and activation of the cytotoxic activity of the drug moiety. The selectivity afforded by drug conjugates minimizes toxicity to normal cells, thereby enhancing tolerability of the drug in the patient.

Any suitable payload known to those skilled in the art in view of the present disclosure can be used in the invention. The payload can be, for example, a drug/agent, a linker, a click reaction partner, etc. According to particular embodiments, the payload can be, for example, a cytotoxic agent, a cytostatic agent, a chemotherapeutic agent, a toxin, a radionuclide, a DNA, an RNA, an siRNA, a microRNA, a peptide nucleic acid, a non-natural amino acid, a peptide, an enzyme, a fluorescent tag, a biotin, a linker, or a first click reaction partner.

As used herein, a "pharmaceutical composition" refers to a composition that includes at least one active pharmaceutical ingredient (API). An example of an API suitable for use in accordance with the present invention is a conjugated antibody or a conjugated Fc fusion protein. Ingredients in a pharmaceutical composition, other than the API(s), may include one or more excipients; preferably, the excipient(s) are substantially or completely pharmaceutically inert.

As used herein, the term "covalently linked" means that the payload is attached to the antibody via at least one covalent linkage. The linkage can be direct, i.e. without a linker, or indirect, i.e. via a linker.

As used herein, the term "linker" refers to a chemical moiety that joins two molecules. Any suitable linker known to those skilled in the art in view of the present disclosure can be used in the invention. The linkers can be, for example, a single covalent bond, a substituted or unsubstituted alkyl, a substituted or unsubstituted heteroalkyl moiety, a polyethylene glycol (PEG) linker, a peptide linker, a sugar-based linker, or a cleavable linker, such as a disulfide linkage or a protease cleavage site such as valine-citrulline-PAB.

As used herein, the term "amine-containing payload" refers to a payload containing one or more reactive amines (e.g., primary amines). For example, the amine-containing payload can comprise an amine donor unit (e.g., primary amine NH2), a linker (e.g., a molecule that is linked to an amine donor unit and contains additional functionality for attachment to a payload such as a small molecule, a polypeptide, or a biocompatible polymer), and an agent moiety (e.g., a payload such as a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, linker or a first click reaction partner). The amine-containing payload can also be a polypeptide (e.g., an antibody) or a biocompatible polymer containing one or more reactive lysine, N-termini, or reactive amines.

The term "drug-to-antibody ratio" or "DAR" refers to the number of drugs, e.g., 3-APA, attached to the antibody of the ADC. The number of drug molecules bound per antibody moiety or the degree of labeling is a parameter commonly used in the art and is designated "DAR" for "drug-antibody ratio". The DAR of an ADC can range from 1 to 8, although higher loads, e.g., 10, are also possible depending on the number of linkage site on an antibody. The term DAR may be used in reference to the number of drugs loaded onto an individual antibody. A DAR2 refers to drug load species of 2. The behavior of the DAR in a biological sample is representative of the stability of the ADC. A decrease in the DAR between two samples is representative of the stability of the ADC.

The term "DOL" or "degree of labeling" refers to the number of labels, e.g., 3-APA, that are covalently conjugated per heavy chain of an antibody of an antibody drug conjugate (ADC). The DOL can range from 1 to 8, although higher loads, e.g., 10, are also possible depending on the number of linkage site on an antibody. The term DOL may be used in reference to the number of drugs loaded onto an individual antibody. A DOL2 refers to a degree of labeling of 2. The degree of labeling is a parameter commonly used in the art. The term "degree of substitution" or "DOS" can be interchangeably used with DOL. The degree of labeling is determined experimentally by mass spectrometry, UV-Vis spectroscopy, or chromatographic methods such as reverse phase HPLC and hydrophobic interaction chromatography. The desired DOL for a site-specific labeling method is often full occupancy of the desired site with no labeling at other sites. For example, for typical antibodies containing two heavy chains and two light chains, where each heavy chain contains a Gln295 conjugation site, the optimal DOL would be a DOL of 2, wherein both Gln295 residues of the antibody have been fully conjugated to a drug molecule.

The term "reactive group" refers to a group that is capable of reacting with another chemical group to form a covalent bond, i.e. is covalently reactive under suitable reaction conditions and generally represents a point of attachment for another substance.

The term "low-ionic strength" or "low salt" conditions are buffer conditions in which the salt concentration of the buffer solution is kept or brought to concentrations below about 30 mM (also referred to herein as "solution of low-ionic strength"). The salt can be a sodium salt, potassium salt, or any kind of other salt. The low salt concentration may be about 25 mM or less, or about 24 mM or less, or about 23 mM or less, or about 22 mM or less, or about 21 mM or less, or about 20 mM or less, or about 19 mM or less, or about 18 mM or less, or about 17 mM or less, or about 16 mM or less, or about 15 mM or less, or about 14 mM or less, or about 13 mM or less, or about 12 mM or less, or about 11.2 mM or less, or about 11 mM or less, or about 10 mM or less. The low salt concentration may be, for example, from about 0.1 mM to about 10 mM, or from about 1 mM to about 10 mM, or from about 2 mM to about 10 mM, or from about 0.1 mM to about 12 mM, or from about 1 mM to about 12 mM, or from about 2 mM to about 12 mM. The low salt concentration may be, for example, 25 mM, 24 mM, 23 mM, 22 mM, 21 mM, 20 mM, 19 mM, 18 mM, 17 mM, 16 mM, 15 mM, 14 mM, 13 mM, 12 mM, 11 mM, 10 mM, 9 mM, 8 mM, 7 mM, 6 mM, 5 mM, 4 mM, 3 mM, 2 mM, 1 mM or 0 mM. The low salt or low-ionic strength condition can be achieved by methods such as, but not limited to, dilution, or buffer exchange methods such as dialysis, diafiltration, filtration, precipitation and/or chromatographic method and/or other methods such as precipitation, or lyophilization. A method of "reducing the ionic strength" of a solution or preparation refers to reducing the salt concentration of said solution or preparation.

"Tm" or "mid-point temperature" "is the temperature midpoint of a thermal unfolding curve. It refers to the temperature where 50% of the amino acid sequence is in its native conformation and the other 50% is denatured. A thermal unfolding curve is typically plotted as a function of temperature. Tm is used to measure protein stability. In general, a higher Tm is an indication of a more stable protein. The Tm can be readily determined using methods well known to those skilled in the art such as Circular Dichroism Spectroscopy, Differential Scanning calorimetry, Differential Scanning Fluorimetry (both intrinsic and extrinsic dye based), UV spectroscopy, FT-IR and Isothermal calorimetry (ITC).

"Tagg" refers to the temperature at which the protein starts to aggregate either through dimerization or oligomerization. The aggregation temperature detects the onset of aggregation, the temperature at which a protein will show a tendency to aggregate. Tagg can be determined by differential scanning calorimetry (DSC), Differential Scanning Fluorimetry (DSF) or by circular dichroism (CD). These techniques can detect small changes in the conformation of the protein and therefore detect the starting point of aggregation. Tagg values can be lower or higher than Tm. In cases where Tagg is lower than Tm, the protein either dimerizes and/or oligomerizes first and then starts unfolding later at higher temperatures than the Tagg. In cases where Tagg is higher than Tm, the protein starts to unfold first and then aggregates at a higher temperature than the Tm. Both events are commonly observed and depend on amino acid composition and protein conformation.

"Q295" or "Gln295" described herein refers to the Fc conjugation site found in the CH2 domain of the antibody constant region. Gln295 are substrates for transglutaminase. As certain antibodies have two heavy chains and two Gln295 residues, transglutaminase antibody conjugation is capable of providing and antibody with conjugates on each Gln295 residue with a drug to antibody ration (DAR) of up to 2.0, The conjugation occurs between glutamine the amine conjugated payload, The linkage between the glutamine and the amine-containing payload is an isopeptide bond of the formula CO—NH—, wherein NH— is linked to a linker and a payload moiety.

"N297" or "Asn297" refers to the heavy chain Fc glycosylation site. In traditional conjugation methods using microbial transglutaminase, this site is deglycosylated prior to conjugation.

As used herein, the term "transglutaminase" refers to an enzyme that catalyzes the formation of an isopeptide bond between a free amine group on a payload and the acyl group on the side chain of a glutamine residue in an antibody or antigen binding fragment thereof. Transglutaminases are protein-glutamine γ-glutamyltransferases (EC 2.3.2.13), which typically catalyze pH-dependent transamidation of glutamine residues with lysine residues. Examples of transglutaminases include, but are not limited to, microbial transglutaminase (mTG), human transglutaminase, tissue transglutaminase (tTG), and Factor XIII Examples of human transglutaminases include, but are not limited to, keratinocyte transglutaminase (Uniprot P22735), tissue transglutaminase (UniProt P21980), epidermal transglutaminase and prostate transglutaminase. These enzymes can be from either natural or recombinant sources. Glutamine and lysine amino acids in a peptide or polypeptide can be substrates for transglutaminase crosslinking. For example, the payload can be linked to a linker comprising a lysine.

The transglutaminase can be any transglutaminase deemed suitable by those of skill in the art. The transglutaminase used in the invention described herein can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, MO) and MP Biomedicals (Irvine, CA)).

In some embodiments, the transglutaminase is derived from a fungal protein (e.g., *Oomycetes, Actinomycetes, Saccharomyces, Candida, Cryptococcus, Monascus,* or *Rhizopus* transglutaminases). In some embodiments, the transglutaminase polypeptide is derived from Myxomycetes (e.g., *Physarum polycephalum* transglutaminase). In some embodiments, the mTGase polypeptide is derived from a bacterial protein, such as transglutaminase from *Streptoverticillium* sp. or *Streptomyces* sp. (e.g., *Streptomyces mobarensis* or *Streptoverticillium mobarensis*). In some embodiments, the transglutaminase polypeptide is derived from a bacterial protein, such as transglutaminase from, but not limited to, *Streptoverticillium mobarensis, Streptoverticillium griseocameum, Streptoverticillium ladakanum, Streptomyces mobarensis, Streptomyces viridis, Streptomyces ladakanum, Streptomyces caniferus, Streptomyces platensis, Streptomyces hygroscopius, Streptomyces netropsis, Streptomyces fradiae, Streptomyces roseovertivillatus, Streptomyces cinnamaoneous, Streptomyces griseocameum, Streptomyces lavendulae, Streptomyces lividans, Streptomyces lydicus, Streptomyces sioyansis, Actinomadura* sp., *Bacillus* (e.g., *Bacillus circulans, Bacillus subtilis,* etc.), *Corynebacterium* ammonia genes, *Corynebacterium glutamicum, Clostridium, Enterobacter* sp., *Micrococcus, Providencia* sp., or isolates thereof. In some embodiments, the transglutaminase is a calcium independent transglutaminase which does not require calcium to induce enzyme conformational changes and allow enzyme activity. In some embodiments, the transglutaminase polypeptide is derived from *S. mobarensis*.

Commercially available calcium independent transglutaminase such as ACTIVA (Ajinomoto, Japan) is also suitable for the present invention. In some embodiments, the transglutaminase used in the invention described herein can also be a recombinant protein produced using recombinant techniques known to persons skilled in the art. In some embodiments, the transglutaminase used in the invention described herein can be a purified protein.

The numbering of amino acid residues in the antibody constant region throughout the specification is according to the EU index as described in Kabat et al. (1991, J Immunol 147(5): 1709-19), unless otherwise explicitly stated.

Conventional one and three-letter amino acid codes are used herein as shown in Table 1.

TABLE 1

Standard amino acids and abbreviations.

| Amino acid | Three- | One- |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Methods of the Invention

In an attempt to help the reader of the application, the description has been separated into various paragraphs or sections or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated.

The embodiments of the invention are intended to be merely exemplary, and those skilled in the art will recognize, or be able to ascertain using no more than routine experimentation, numerous equivalents to the specific procedures of the invention. All such equivalents are considered to be within the scope of the present invention and are covered by the following claims.

Monoclonal antibodies (mAbs) are being increasingly used for targeting drug delivery due to their high selectivity for tumor-associated antigens, favorable pharmacokinetics and relative low intrinsic toxicity. Antibody drug conjugates (ADC) are formed by covalently linking anticancer drugs to mAb, usually through a stable linker system to a particular site on the mAbs. Glutamine 295 (Q295) located in the CH2 domain of the Fc heavy chain of mAb is a commonly used conjugation site. The conjugation is typically done using a microbial transglutaminase (MTG) that will catalyze the formation of a stable isopeptide bond between the glutamine side chain and a free amine of a cytotoxic agent.

A major issue in ADC manufacturing is the attachment of the cytotoxic agent to the antibody in a way that allows tight control over conjugation site, conjugation rates and the degree of labeling (DOL). The conjugation product is often a rather heterogeneous mixture relative to its DOL which not only complicates the development of the ADC but can also lead to suboptimal therapeutic window of the final drug.

Antibodies are often glycosylated at residue N297, near the Q295 conjugation site. It is known that removal of the antibody glycan leads to increased mobility of the C'D/E strand as demonstrated by H-D exchange (Houde D. et al. Anal Chem (2009), 81(7): 2644). Additionally, it has been demonstrated that reactivity with MTG correlates with protease susceptibility (Spolaore et al., 2012, Biochemistry 51(43):8679-8689), likely also an indicator of backbone flexibility. The steric effect of the glycan molecules at N297 is believed to hinder conjugation at Q295. Glycosylation at residue N297 will interfere with transglutaminase conjugation at Q295 and affect degrees of labeling (DOLs) or drug-to-antibody ratios (DARs). As a result, conjugation of glycan intact antibodies under traditional buffer conditions will produce a product with lower degree of labeling and reduced efficacy.

In traditional conjugation methods known in the art, the antibody is deglycosylated or aglycosylated at N297 to allow conjugation at Q295. The resulting antibody, without interfering glycosylation, is then suitable to treatment with microbial transglutaminase (MTG) and able to react with a primary amine compound to produce a glutamyl-modified antibody.

As traditional conjugation methods require an initial deglycosylation step, they have historically led to antibodies with less favorable manufacturability as removal of glycans abrogates interaction of the antibody with Fc receptors. Fc glycans are critical for maintaining structural integrity, communication with the Fc receptor and the downstream immunological response. The presence and structure of N-linked glycan at N297 in particular, is understood to be needed for activation of the effector function by an immune complex. Conjugated antibodies generated through traditional conjugation methods requiring deglycosylated antibody or glycan-engineered antibody will typically have reduced activity and/or reduced stability due to the glycan modification content. For example, the antibody may lose stability, affinity or selectivity.

The invention described herein provides a method of conjugating a glycosylated antibody, therefore allowing for the generation of antibody drug conjugates that are more suitable for manufacturing. The present invention provides conditions that provide desired DOL and are applicable to any reactive species or antibody. The conditions of the invention do not require glycan-engineering or glycan removal.

Traditional microbial transglutaminase conjugation methods using deglycosylated or glycan-engineered antibodies are generally performed under traditional buffer conditions such as PBS or buffer with similar ionic strength. Existing methods used to modulate the degree of labeling (DOL) generally depend upon alteration of the concentration of the carrier molecule or alteration of the concentration of the reactive labeling species. The DOL may also vary depending on the chemical nature of the reactive species. However, such alterations have typically very little effect on the DOL when used on glycan intact antibodies. In contrast to known procedures, the low-ionic strength condition of the present invention allows for site-specific conjugation of antibodies with an amine compound or amine containing payload using transglutaminase, providing desired DOL without the need for a preliminary deglycosylation step and removal of the antibody glycans, therefore allowing for antibody drug conjugates with better manufacturability.

In certain embodiments, the primary amine compound comprises a reactive group capable of further reaction after transglutamination. In some embodiments, the glutamyl-modified antibody can be reacted with a reactive payload compound to form an antibody payload conjugate. In certain embodiments, the primary amine compound comprises an azide.

In certain embodiments, the methods of the invention may provide numerous advantages over traditional conjugation methods, including improved recovery as deglycosylation and subsequent purification are not necessary; and improved stability, as deglycosylation was shown to decrease the $T_m$ and $T_{agg}$ values for the antibody.

In certain embodiments, the invention provides a method of producing a conjugated antibody or a conjugated Fc fusion protein comprising reacting a glycosylated antibody or a glycosylated Fc fusion protein with an amine compound in the presence of transglutaminase in low-ionic strength conditions. The glycosylated antibody or the glycosylated Fc fusion protein comprises N-linked glycan at amino acid Asn297. Preferably, the glycosylated antibody or the glycosylated Fc fusion protein has intact glycan content. Preferably, the glycosylated antibody or the glycosylated Fc fusion protein was not subject to treatment with endo or exo-glycosidase prior to reacting the glycosylated antibody or glycosylated Fc fusion protein with an amine compound in the presence of transglutaminase in low-ionic strength conditions. Preferably, the glycosylation sites of the glycosylated antibody or the glycosylated Fc fusion protein were not glycan-engineered or glycan-modified prior to reacting the glycosylated antibody or glycosylated Fc fusion protein with an amine compound in the presence of transglutaminase in low-ionic strength conditions.

In certain embodiments, the antibody used in the method of the invention is a glycosylated antibody or glycosylated Fc fusion protein, with partially modified or partially engineered glycans, but that still retains N-linked glycan at amino acid Asn297.

According to certain embodiments, the glycosylated antibody has G0F, G1F, G2F, G0, G1, or G2 glycans.

In certain embodiments, the antibody can be any from known to those of skill in the art. In some embodiments, the antibody comprises an IgA1, IgA2, IgD, IgE, IgG1, IgG2, IgG3, IgG4, or IgM heavy chain. In some embodiments the antibody comprises a kappa or lambda light chain. In some embodiments, the antibody is a monoclonal antibody. In some embodiments, the antibody is a polyclonal antibody. In some embodiments, the antibody is a bispecifc or multipsecific antibody. In some embodiments, the antibody is a chimeric antibody, a humanized antibody or a human antibody.

In certain embodiments, the amine compound is an amine containing payload comprising one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, imaging agent, or a first click reaction partner.

In certain embodiments, the method of producing the conjugated antibody or the conjugated Fc fusion protein in low-ionic strength conditions is conducted in a solution comprising a salt concentration of about 25 mM or less, or about 20 mM or less, or about 15 mM or less, or about 10 mM or less.

In another embodiment of the invention, the conjugation reaction is conducted in water buffered with but not limited to phosphate, acetate or Tris. In alternative embodiments, the solution of low-ionic strength comprises sodium phosphate, potassium phosphate, HEPES, sodium acetate, or Tris.

In certain embodiments of the invention, the conjugation reaction is conducted in low-ionic strength conditions comprising 10 mM or less of sodium phosphate, potassium phosphate, sodium acetate, or Tris.

In certain embodiments of the invention, the conjugation reaction is conducted under low-ionic strength conditions comprising 10 mM or less of potassium phosphate, 10 mM or less of sodium phosphate, 10 mM or less of sodium acetate, or 10 mM or less of Tris.

In another embodiment of the invention, the method further comprises reducing the ionic strength of the antibody or antibody preparation to provide a low-ionic strength antibody preparation prior to reacting with the amine compound, i.e., the method of producing the conjugated antibody or the conjugated Fc fusion protein comprises reducing the ionic strength of a solution containing the glycosylated antibody or the glycosylated Fc fusion protein to provide the low-ionic strength conditions.

In another embodiment of the invention, the method further comprises reducing the ionic strength of the transglutaminase preparation to provide a low-ionic strength transglutaminase preparation prior to reacting with the amine compound, i.e., the method of producing the conjugated antibody or the conjugated Fc fusion protein further comprises reducing the ionic strength of a solution containing the transglutaminase to provide the low-ionic strength conditions.

In another embodiment, the ionic strength is reduced by dilution, or buffer exchange through dialysis, diafiltration, filtration, precipitation and/or chromatographic method. In embodiments of the conjugation method, salt(s) and/or additives are removed by methods such as dilution or buffer exchange through dialysis, diafiltration, filtration, precipitation and/or a chromatography method, suitable chromatography methods including gel permeation, size exclusion chromatography, ion exchange chromatography, or affinity chromatography. The removal of salt(s) and or additive(s) can be done using dialysis membrane tubings, centrifugal devices with porous membranes sized to retain the protein, but allowing the buffer to pass, and/or chromatography supports. Alternatively or additionally, removal of the salt(s) and/or additive(s) can be by precipitation or lyophilization. The concentration of the salt or additive is preferably reduced before the start of the conjugation reaction. Ideally, the concentration of the salt(s) and/or additives is reduced to a level that would permit the conjugation of the conjugate without removal and/or engineering of the glycan content of the antibody. Ideally, the concentration of the salt(s) and/or additives is reduced to a level that would permit 90% or more of the antibody to be conjugated to one amine-containing payload per heavy chain.

According to an embodiment, a method of producing a conjugated antibody or a conjugated Fc fusion protein comprising reacting a glycosylated antibody or a glycosylated Fc fusion protein with an amine compound in the presence of transglutaminase in low-ionic strength conditions sufficient to achieve from 80-100% or from 90-100% conversion of said glycosylated antibody or said glycosylated Fc fusion protein to an antibody or Fc fusion protein, respectively, conjugated to one amine-containing payload per heavy chain (e.g., a DOL of 2).

In other embodiments of the invention, the transglutaminase is a microbial transglutaminase. As described above, the transglutaminase can be any transglutaminase deemed suitable by those of skill in the art.

In some aspect of the invention, the reaction is conducted for at least 18 hours. In other aspects of the invention, the reaction is conducted for at least 24 hours. In certain embodiments, the amine compound is a primary amine compound comprising and azide. In some embodiments, the primary amine compound comprises a reactive group or protected reactive group. The reactive group and protected reactive group can be any group deemed suitable by someone of skill in the art. In certain embodiments, the reactive group is capable of forming a covalent bond with a reactive payload compound. Useful reactive groups include azides, alkynes, cycloalkynes, thiols, alcohols, ketones, aldehydes, acids, esters, hydrazides, anilines, tetrazines, cyclooctenes, cyclopropenes, In certain embodiments, the primary amine group comprises a carboxyl and the reactive payload comprises an amine.

In another embodiment, the method further comprising reacting the conjugated antibody with a reactive payload compound to form an antibody-payload conjugate. The payload of the reactive payload compound can be any payload deemed suitable in those of skill in the art. In particular embodiments, the payload is provided in the form of a reactive payload compound comprising a reactive group capable of forming a covalent bond with a reactive group on the primary amine compound. Reactive groups for the reactive payload compound include azides, alkynes, cycloalkynes, thiols, alcohols, ketones, aldehydes, acids, esters, hydrazides, anilines, and amines.

In some aspects of the invention, the method of the invention provides a degree of labeling (DOL) of at least 1.8.

In some aspects of the invention, the method of the invention provides a degree of labeling (DOL) of at least 1.9.

In some aspects of the invention, the method of the invention provides a degree of labeling (DOL) of 2.

In some aspects of the invention, the method of the invention provides a drug to antibody ratio (DAR) of 2.0.

In some aspect of the invention, 90% or more of the antibody or Fc fusion protein generated by the method of the invention is conjugated to 2 amine-compounds.

In some aspect of the invention, 95% or more of the antibody or Fc fusion protein generated by the method of the invention is conjugated to 2 amine-containing payloads.

In some aspect of the invention, 100% of the antibody or Fc fusion protein generated by the method of the invention is conjugated to 2 amine-containing payloads.

In certain embodiments, the conjugation occurs in the Fc domain of the antibody.

In certain embodiments, the conjugation occurs at Gln295.

In certain embodiments, the method of the invention provides an antibody conjugated to an amine-containing payload, through a linker at Gln295 preferably, and the payload comprises one or more reagent selected from the group consisting of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, and a first click reaction partner. In some embodiments, the cytotoxic agent includes any agent that is detrimental to the growth, viability or propagation of cells. The payload can also comprise a chelator or a radionuclide. Exemplary radionuclides include, but are not limited to $^{225}$Ac, $^{212}$Bi, $^{131}$I, $^{211}$At, $^{227}$Th and $^{186}$Re.

In certain embodiments, the amine compound is an amine containing payload comprising one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, and a first click reaction partner.

In certain embodiments, the amine-containing payload comprises the first click reaction partner, preferably, the method further comprises reacting the antibody-payload conjugate with a second click reaction partner that comprises one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, and biotin to obtain a second antibody-payload conjugate.

In certain embodiments, the first click reaction partner is 3-azido-1-propylamine, and the second click reaction partner is DBCO-val-cit-MMAF or DBCO-MMAF.

Examples of click chemistry methods suitable for use in accordance with the invention are described, for example, in PCT/US2018/065913, which is incorporated by reference herein.

ENUMERATED EMBODIMENTS

Provided below are exemplary numbered embodiments of the present invention:

1. A method of producing a conjugated antibody or a conjugated Fc fusion protein comprising reacting a glycosylated antibody or a glycosylated Fc fusion protein with an amine compound in the presence of transglutaminase in low-ionic strength conditions.
2. The method according to embodiment 1, wherein the glycosylated antibody or the glycosylated Fc fusion protein has intact glycan content.
3. The method according to embodiment 1 or 2, wherein the amine compound is an amine containing payload comprising one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, biotin, imaging agent, or a first click reaction partner.
4. The method according to any of embodiments 1-3, wherein the glycosylated antibody or the glycosylated Fc fusion protein was not subject to treatment with endo or exo-glycosidase prior to reacting the glycosylated antibody or the glycosylated Fc fusion protein with the amine compound in the presence of the transglutaminase in the low-ionic strength conditions.
5. The method according to any of embodiments 1-4, wherein the glycosylation sites of the glycosylated antibody or the glycosylated Fc fusion protein were not glycan-engineered or glycan-modified prior to reacting the glycosylated antibody or the glycosylated Fc fusion protein with the amine compound in the presence of the transglutaminase in the low-ionic strength conditions.
6. The method according to any of embodiments 1-5, wherein the glycosylated antibody or the glycosylated Fc fusion protein contains N-linked glycans at amino acid Asn297.
7. The method according to any of embodiments 1-6, wherein the method of producing the conjugated antibody or the conjugated Fc fusion protein in low-ionic strength conditions is conducted in a solution comprising a salt concentration of about 25 mM or less.
8. The method according to any of embodiments 1-6, wherein the method of producing the conjugated antibody or the conjugated Fc fusion protein in low-ionic strength conditions is conducted in a solution comprising a salt concentration of about 20 mM or less.
9. The method according to any of embodiments 1-6, wherein the method of producing the conjugated antibody or the conjugated Fc fusion protein in low-ionic strength conditions is conducted in a solution comprising a salt concentration of about 15 mM or less.
10. The method according to any of embodiments 1-6, wherein the method of producing the conjugated antibody or the conjugated Fc fusion protein in low-ionic strength conditions is conducted in a solution comprising a salt concentration of about 10 mM or less.
11. The method of any one of embodiments 7-10, wherein the solution of low-ionic strength comprises sodium phosphate, potassium phosphate, HEPES, sodium acetate, or Tris.
12. The method of embodiment 11, wherein the solution of low-ionic strength comprises potassium phosphate.
13. The method of embodiment 11, wherein the solution of low-ionic strength comprises sodium phosphate.
14. The method of embodiment 11, wherein the solution of low-ionic strength comprises HEPES.
15. The method of embodiment 11, wherein the solution of low-ionic strength comprises Tris.
16. The method of embodiment 11, wherein the solution of low-ionic strength comprises sodium actetate.
17. The method according to any of embodiments 1-16, wherein the method of producing the conjugated antibody or the conjugated Fc fusion protein further comprises reducing the ionic strength of a solution containing the glycosylated antibody or the glycosylated Fc fusion protein to provide the low-ionic strength conditions.
18. The method according to any of embodiments 1-17, wherein the method of producing the conjugated antibody or the conjugated Fc fusion protein further comprises reducing the ionic strength of a solution containing the transglutaminase to provide the low-ionic strength conditions.
19. The method according to either of embodiments 17 or 18, wherein the ionic strength is reduced by dilution, or buffer exchange through dialysis, diafiltration, filtration, precipitation and/or chromatographic methods.
20. The method according to any of embodiments 1-19, wherein the transglutaminase is a microbial transglutaminase.
21. The method according to any of embodiments 1-20, wherein the amine compound is a primary amine compound.
22. The method of embodiment 21, wherein the primary amine compound comprises an azide.
23. The method according to any of embodiments 1-22, wherein the method of producing the conjugated antibody or the conjugated Fc fusion protein further comprises reacting the conjugated antibody with a reactive payload compound to form an antibody-payload conjugate.
24. The method according to any of embodiments 1-23, wherein the method of producing the conjugated antibody or the conjugated Fc fusion protein provides an average degree of labeling (DOL) of at least 0.9 per heavy chain.

25. The method of embodiment 24, wherein the method of producing the conjugated antibody or the conjugated Fc fusion protein provides an average degree of labeling (DOL) of 1 per heavy chain.
26. The method according to any of embodiments 1-23, wherein the method of producing the conjugated antibody or the conjugated Fc fusion protein provides a DOL of at least 1.8 per antibody.
27. The method of embodiment 26, wherein the method of producing the conjugated antibody or the conjugated Fc fusion protein provides a DOL of 2.0 per antibody.
28. The method according to any of embodiments 1-23, wherein 80% or more of said glycosylated antibody or said glycosylated Fc fusion protein is converted to said conjugated antibody or said conjugated Fc fusion protein, respectively, with a DOL of 2 (i.e., antibody species or conjugated Fc fusion protein species with a DOL of 2).
29. The method according to any of embodiments 1-23, wherein 90% or more of said glycosylated antibody or said glycosylated Fc fusion protein is converted to said conjugated antibody or said conjugated Fc fusion protein, respectively, at a DOL of 2.
30. The method according to any of embodiments 1-23, wherein 100% of said glycosylated antibody or glycosylated Fc fusion protein is converted to said conjugated antibody or said conjugated Fc fusion protein, respectively, at a DOL of 2.
31. The method according to any of embodiments 1-23, wherein the method of producing the conjugated antibody or the conjugated Fc fusion protein provides less than 10% side product, relative to said conjugated antibody or said conjugated Fc fusion protein, respectively.
32. The method of any one of embodiments 24-30, comprising determining the degree of labeling (DOL) by LC-MS.
33. The method according to any of embodiments 1-32, wherein the conjugated antibody or the conjugated Fc fusion protein is conjugated at its Fc domain.
34. The method of embodiment 33, wherein the conjugated antibody or the conjugated Fc fusion protein is conjugated at Gln295.
35. The method according to any of embodiments 1-32, wherein the conjugated antibody or the conjugated Fc fusion protein is conjugated to an amine-containing payload, through a linker at Gln295, and the payload comprises one or more reactive groups selected from the group consisting of a cytotoxic agent, cytostatic agent, chemotherapeutic agent, toxin, radionuclide, chelator, DNA, RNA, siRNA, microRNA, peptide nucleic acid, non-natural amino acid, peptide, enzyme, fluorescent tag, biotin, imaging agent, and a first click reaction partner.
36. The method of embodiment 35, wherein the amine-containing payload comprises the first click reaction partner, and the method further comprises reacting the conjugated antibody or the conjugated Fc fusion protein with a second click reaction partner that comprises one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, imaging agent, or biotin to obtain a second conjugate.
37. The method of embodiment 36, wherein the first click reaction partner is 3-azido-1-propylamine, and wherein the second click reaction partner is DBCO-val-cit-MMAF or DBCO-MMAF.
38. The method according to any of embodiments 1-37 for producing a conjugated antibody, wherein the method comprises reacting the glycosylated antibody with the amine compound in the presence of the transglutaminase in the low-ionic strength conditions.
39. The method according to any of embodiments 1-37 for producing a conjugated Fc fusion protein, wherein the method comprises reacting the glycosylated Fc fusion protein with the amine compound in the presence of the transglutaminase in the low-ionic strength conditions.
40. A conjugated antibody that is made according to the method of any of embodiments 1-38.
41. A pharmaceutical composition comprising the conjugated antibody of embodiment 40.
42. A conjugated Fc fusion protein that is made according to the method of any of embodiments 1-37 or 39.
43. A pharmaceutical composition comprising the conjugated Fc fusion protein of embodiment 42.

The following examples of the invention are provided to further illustrate certain embodiments. It should be understood that the following examples do not limit the scope of the invention.

EXAMPLES

Antibodies used in the examples below are commercially available and include trastuzumab (Herceptin®), pertuzumab (Perjeta®) and panitumumab (Vectibix®). Trastuzumab and pertuzumab bind to human Her2. Panitumumab binds to human EGFR.

Example 1: Conjugation of Trastuzumab with 3-APA Under Low-Ionic Strength Conditions Using Microbial Transglutaminase (MTG) from Zedira Antibody and Transglutaminase Preparation A proprietary recombinant Microbial transglutaminase (MTG or BTG for bacterial transglutaminase) produced in E. coli was purchased from Zedira (catalog number T001). The lyophilized powder was resuspended in water and buffer exchanged into a low-ionic strength buffer (such as 10 mM potassium phosphate buffer pH 7.2) with a Zeba desalting column (Thermo Fisher). Trastuzumab, a humanized IgG1 antibody, was also buffer exchanged into low-ionic strength buffer (such as 10 mM potassium phosphate) using a Zeba desalting column. Buffer exchanged Trastuzumab and microbial transglutaminase were then diluted with water or the appropriate buffer for the desired reaction condition to reach the final concentrations of 1 mg/mL for the mAb and 10 U/mg for the enzyme. The antibody and the enzyme were incubated with 20-100× molar excess relative to mAb of 3-azido propylamine (3-APA) substrate, an azido-containing reagent with reactivity suitable for payload attachment.

Conjugation Reaction

Reactions were stopped at the indicated time points by the addition of C102, a MTG-blocker from Zedira that irreversibly alkylates the active site cysteine of microbial transglutaminase. The final concentration of the MTG-blocker used was 100 uM. For intact mass analysis, mAbs were deglycosylated with Rapid PNGase F (2% v/v) to reduce the heterogeneity of the sample and facilitate analysis; dithiothreitol or TCEP were added for reduced mass analysis.

LC-MS was performed on an Agilent 1260 HPLC system connected to an Agilent G6224 MS-TOF Mass Spectrometer. LC was run on an Agilent RP-mAb C4 column (2.1×50 mm, 3.5 micron) at a flow rate of 1 mL/min with the mobile phase 0.1% formic acid in water (A) and 0.1% formic acid in acetonitrile (Sigma-Aldrich Cat #34688) (B) and a gradient of 20% B (0-2 min), 20-60% B (2-3 min), 60-80% B (3-5.5 min). The instrument was operated in positive electrospray ionization mode and scanned from m/z 600 to 6000. Instrument settings included: capillary voltage 3500V; fragmentor 175V; skimmer 65V; gas temperature 325 C; drying gas flow 5.0 L/min; nebulizer pressure 30 psig; acquisition mode range 100-7000 with 0.42 scan rate.

Mass to charge spectrum were deconvoluted using the Maximum Entropy algorithm and the degree of labeling (DOL) of each reaction was estimated using relative intensities of the deconvoluted masses corresponding to intact mAb or mAb heavy chain with the addition of multiples of 83 Da (corresponding to 3-APA).

FIG. 1 shows the rate of MTG-catalyzed conjugation of 3-APA to intact and deglycosylated trastuzumab in different reaction buffer compositions. The rate of conjugation in PBS buffer for deglycosylated mAb was very fast and the reaction reached completion within 3 hours. The rate of conjugation of deglycosylated mAb appeared to be even faster in 10 mM phosphate buffer. The conjugation rate for glycan-intact mAb was slow in PBS, reaching only 25% conversion in 5 hours and progressing to 40-60% conversion overnight (data not shown). The conjugation of glycan-intact mAb in 5 or 10 mM phosphate buffer however was significantly faster than in PBS buffer, and reached around 70-80% completion after 5 hours and complete or near-complete conversion after longer incubation times (data not shown). The reaction conducted under low-ionic strength conditions showed an increased conjugation rate relative to the reaction conducted in PBS. Both 10 mM and 5 mM phosphate buffer showed significant rate enhancement compared to PBS (8 mM sodium phosphate, 1.5 mM potassium phosphate, 2.7 mM KCl, 138 mM NaCl).

The transglutaminase reaction was tested under a panel of various buffer conditions with the human IgG1 antibody trastuzumab at 1 mg/mL; 3-APA at 100 molar excess (690 uM); and Zedira transglutaminase (catalog #T001) at 10 U/mg of antibody. Table 2 shows the fraction of fully modified (to DOL=2) glycan intact WT human trastuzumab after 18-20 hours incubation with MTG and 3-APA at 37° C. in a series of reaction conditions. A number of low-ionic strength formulations showed increased modification, and in many cases allowed for complete or nearly complete modification.

TABLE 2

Fraction of DOL = 2 species produced by MTG-catalyzed conjugation under a range of buffer conditions.

| Antibody | Buffer | % DOL = 2 |
|---|---|---|
| Trastuzumab* (deglycosylated) | PBS | 92 ± 0.7% |
| Trastuzumab* (intact) | PBS | 43 ± 1.3% |
| Trastuzumab | water | 95% |
| Potassium Phosphate pH 7.2 | | |
| Trastuzumab | 2.2 mM | 97% |
| Trastuzumab | 6.2 mM | 97% |
| Trastuzumab | 11.2 mM | 93% |
| Trastuzumab | 51.2 mM | 60% |
| Trastuzumab | 151.2 mM | 36% |
| Potassium Phosphate pH 8.0 | | |
| Trastuzumab | 2.2 mM | 92% |
| Trastuzumab | 6.2 mM | 83% |
| Trastuzumab | 11.2 mM | 72% |
| Trastuzumab | 51.2 mM | 41% |
| Trastuzumab | 151.2 mM | 38% |
| Potassium Phosphate pH 5.8 | | |
| Trastuzumab | 2.2 mM | 93% |
| Trastuzumab | 6.2 mM | 84% |
| Trastuzumab | 11.2 mM | 81% |
| Trastuzumab | 51.2 mM | 47% |
| Trastuzumab | 151.2 mM | 33% |
| Hepes pH 7.2 | | |
| Trastuzumab | 2.2 mM | 93% |
| Trastuzumab | 6.2 mM | 95% |
| Trastuzumab | 11.2 mM | 87% |
| Trastuzumab | 51.2 mM | 85% |
| Trastuzumab | 151.2 mM | 50% |
| Hepes pH 8.0 | | |
| Trastuzumab | 2.2 mM | 95% |
| Trastuzumab | 6.2 mM | 93% |
| Trastuzumab | 11.2 mM | 73% |
| Trastuzumab | 51.2 mM | 57% |
| Trastuzumab | 151.2 mM | 47% |
| TRIS pH 7.2 | | |
| Trastuzumab | 2.2 mM | 99% |
| Trastuzumab | 6.2 mM | 95% |
| Trastuzumab | 11.2 mM | 92% |
| Trastuzumab | 51.2 mM | 57% |
| Trastuzumab | 151.2 mM | 32% |
| TRIS pH 8.0 | | |
| Trastuzumab | 2.2 mM | 90% |
| Trastuzumab | 6.2 mM | 96% |
| Trastuzumab | 11.2 mM | 95% |
| Trastuzumab | 51.2 mM | 80% |
| Trastuzumab | 151.2 mM | 43% |
| TRIS pH 9.2 | | |
| Trastuzumab | 2.2 mM | 88% |
| Trastuzumab | 6.2 mM | 85% |
| Trastuzumab | 11.2 mM | 78% |
| Trastuzumab | 51.2 mM | 70% |
| Trastuzumab | 151.2 mM | 63% |
| Sodium Acetate pH 3.6 | | |
| Trastuzumab | 2.2 mM | 0% |
| Trastuzumab | 6.2 mM | 0% |
| Trastuzumab | 11.2 mM | 0% |
| Trastuzumab | 51.2 mM | 0% |
| Trastuzumab | 151.2 mM | 0% |
| Sodium Acetate pH 4.2 | | |
| Trastuzumab | 2.2 mM | 100% |
| Trastuzumab | 6.2 mM | 34% |
| Trastuzumab | 11.2 mM | 0% |
| Trastuzumab | 51.2 mM | 0% |
| Trastuzumab | 151.2 mM | 0% |
| Sodium Acetate pH 5.6 | | |
| Trastuzumab | 2.2 mM | 98% |
| Trastuzumab | 6.2 mM | 99% |
| Trastuzumab | 11.2 mM | 96% |
| Trastuzumab | 51.2 mM | 69% |
| Trastuzumab | 151.2 mM | 47% |

DOL was determined by LC-MS using intact mass analysis.
*Denotes an average of 3 replicates.

Reactions conducted in potassium phosphate buffer at pH 5.8, 7.2, or 8.0, in HEPES at pH 7.2 or 8.0, in Tris buffer at pH 7.2, 8.0 or 9.2, and in sodium acetate buffer at pH 5.6 under low-ionic strength conditions yielded increased modification of the mAb with 3-APA. In all cases, complete or nearly complete conversion of the mAb to the DOL=2 species was achieved at 2.2 mM buffer after 16-20 hours at 37° C. In many cases complete conjugation (reactions achieving a DOL of 2) was achieved at 6.2 and 11.2 mM, and in these cases the low-salt conditions produced significantly more conjugate than PBS or other higher ionic strength reaction conditions. Under low pH conditions (pH 3.6 and 4.2), in sodium acetate buffer, limited product was made under most of the conditions tested—likely because of non-optimal pH conditions for MTG. One exception was the 2.2 mM sodium acetate, pH 4.2 reaction that yielded complete modification of the mAb with 3-APA, which may be explained by the limited buffering capacity failing to maintain the low pH.

Peptide Mapping

Peptide mapping experiments were conducted on the resulting conjugate to identify the conjugation site. 50 µg of the mAb in 50 µL PBS were mixed with 150 µL of 8 M GuHCl, 4 mM EDTA and 30 mM DTT at pH 8.0 and incubated at 37° C. for 1 hour. Cysteines were alkylated by adding 24 µL of 0.5M iodoacetamide (IAA) and incubating the reaction mix for 1 hour at room temperature in the dark. The mAb was then exchanged into 50 mM Tris, 1 mM $CaCl_2$), pH 8.0 using a Zeba spin column (Thermo) and then divided into a 90 µl solution for trypsin digest and a 130 µl solution for digestion with chymotrypsin. 15 µL of 0.1 mg/ml trypsin/Lys-C (Promega #V507) or 0.1 mg/mL chymotrypsin in 1 mM HCl were added and the samples were incubated at 37° C. for 4 hours for trypsin/Lys-C digestion or at room temperature in the dark for 4 hours for chymotrypsin digestion. The LC-MS/MS data were acquired on a SCIEX Triple TOF 6600. The data were processed using Protein Metrics software, Byos (version 3.5-10×64). The peptide mapping experiment demonstrated that the modification was localized at Gln295 (FIG. 2A-2D).

Biophysical Characterization of the Conjugate

Melting Temperature and Aggregation Temperature

Figure 3A:
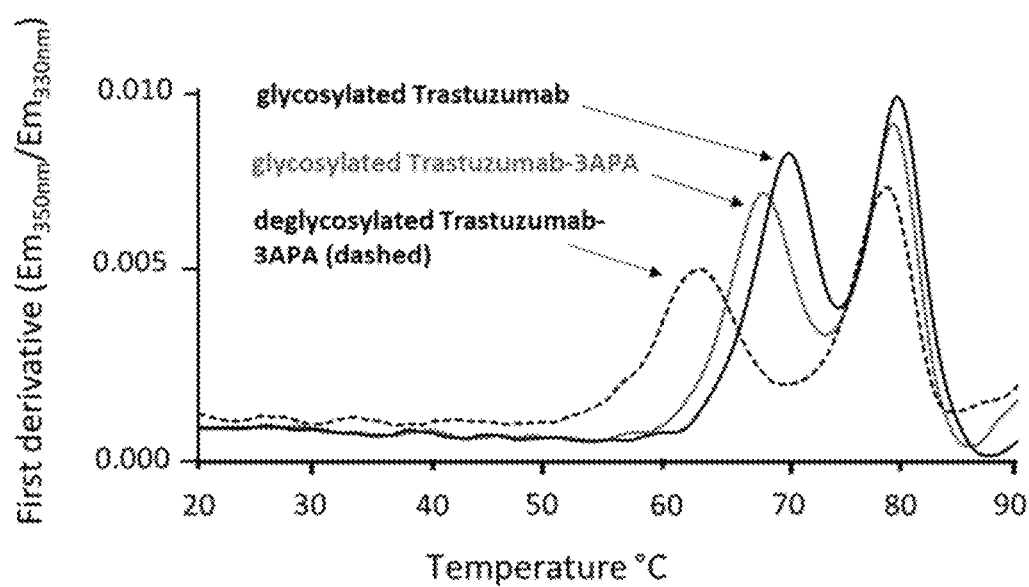
FIG. 3A shows the melting temperature of intact trastuzumab (glycosylated trastuzumab) compared to azide-conjugated trastuzumab (glycosylated trastuzumab-3APA) produced by the low-ionic strength method and azide-conjugated trastuzumab produced by the deglycosylation method.
Figure 3B:
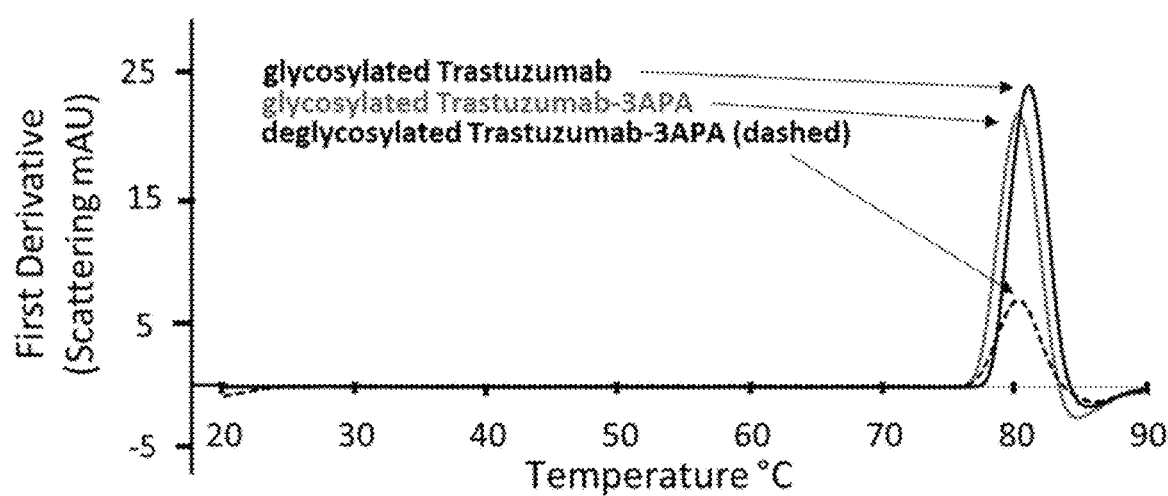
FIG. 3B shows the aggregation temperature of intact trastuzumab (glycosylated trastuzumab) compared to azide-conjugated trastuzumab (glycosylated trastuzumab-3APA) produced by the low-ionic strength method and azide-conjugated trastuzumab produced by the deglycosylation method.

Biophysical characterization of the conjugated Trastuzumab was performed to determine the effect of conjugation on the stability of the antibody. The data was compared to the non-conjugated wild-type (WT) Trastuzumab. The temperature of unfolding ($T_m$) (FIG. 3A) and the temperature of aggregation ($T_{agg}$) (FIG. 3B) were determined in PBS by differential scanning fluorimetry using the Prometheus nanoDSF instrument from Nanotemper. Tm was determined by monitoring changes in fluorescence intensity at 330 and 350 nm upon thermal scanning from 20 to 95° C., and Tagg was determined by monitoring the scattering. The Tm of the Trastuzumab azide conjugate were determined to be 68.3° C. for the first transition (corresponding to the CH2 domain)—a shift of 2.1° C. relative to the glycosylated WT mAb; and 79.2° C. for the second transition (corresponding to the Fab), a shift of 0.3° C. relative to glycosylated wild type mAb. In contrast, deglycosylation of trastuzumab reduced the Tm of the CH2 domain by ~8° C. The aggregation temperature (Tagg) of the glycosylated Trastuzumab conjugate and the deglycosalted Trastuzumab conjugate were similar with a Tagg of 77.7° C. but were 1.1° C. lower when compared to the glycosylated non-conjugated Tratuzumab (Table. 3).

TABLE 3

| | $T_m$ (first transition) | $T_m$ (second transition) | $T_{agg}$ |
|---|---|---|---|
| Glycosylated Trastuzumab | 70.4 | 79.5 | 78.8 |
| Glycosylated Trastuzumab - 3APA produced under low salt | 68.3 | 79.2 | 77.7 |
| Deglycosylated Trastuzumab - 3APA produced under traditional conditions | 62.7 | 78.6 | 77.7 |

Analytical Size Exclusion Chromatography (SEC)

The oligomerization state of conjugated mAb was determined by analytical size-exclusion chromatography for both the azide-modified mAb as well as a conjugate mAb in which the drug payload DBCO-val-cit-MMAF was attached to the azide-modified mAb. In both cases, the elution profile essentially matched unconjugated trastuzumab and was consistent with 100% monomer.

Activity of the Conjugate

Figure 4:
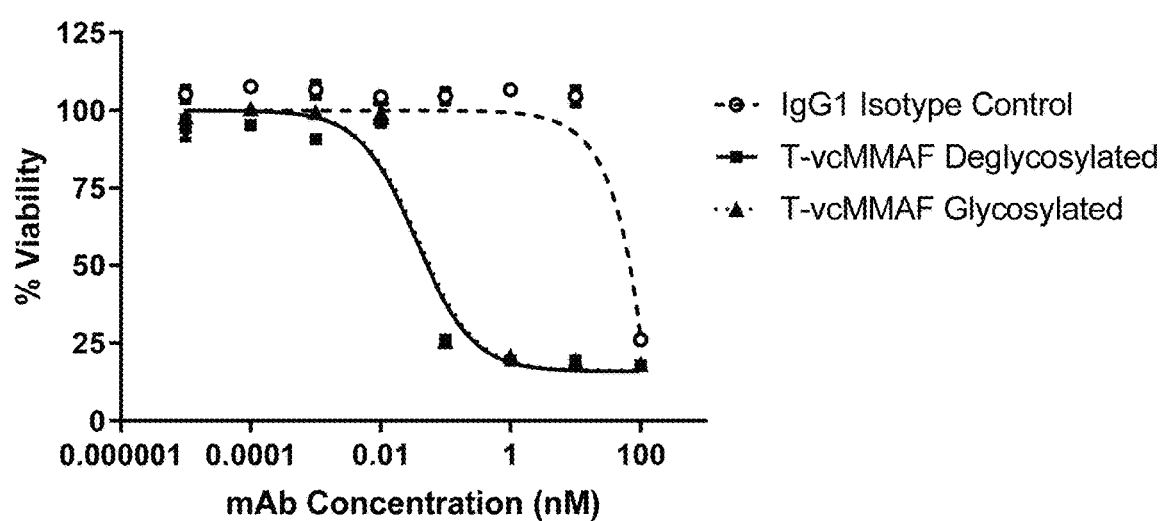
FIG. 4 compares the cell killing activity of trastuzumab-Val-Cit-MMAF (T-vcMMAF) drug conjugates produced either with deglycosylated trastuzumab via established transglutaminase methods or under low salt reaction conditions using glycan-intact mAb. SK-BR3 cells were treated with varying concentrations of conjugate for 72 hrs, and cell killing was determined by Cell Titer Glo assay.

To demonstrate that the activity of conjugates produced under low-ionic strength condition on glycosylated mAb is comparable to conjugates produced by established methods, the azido-mAb produced under low-salt conditions was conjugated to drug payload and the activity was demonstrated in cell assays (FIG. 4). Trastuzumab was conjugated to 3-APA under low salt conditions as described above, or was deglycosylated with 1 U/mL Rapid PNGase F (New England Biolabs) overnight at 37 C followed by reaction with 3-APA (100-fold molar excess) and MTG (Activa TI, 5-20% w/v or Zedira, 5-20 units/mg of mAb) in PBS buffer at 37° C. for 2-4 hours. The DBCO-Val-Cit-PABC-MMAF drug payload was added to the azide-conjugated mAbs in 10-fold molar excess and allowed to react by strain-promoted click chemistry (SPAAC) for 2-6 hours at room temperature. Free drug was removed from the resulting ADCs using a Zeba desalting column (Thermo).

SKBR3 cells, a high-Her2 cell line, were treated with varying concentrations of the ADCs for 72 hours at 37° C. Cell Titer Glo was used to determine cell viability at the conclusion of the treatment. The cell killing activity of trastuzumab-vcMMAF produced by traditional conjugation methods including a deglycosylation step were found to be similar to the cell activity of trastuzumab-vcMMAF produced under low-ionic strength condition with glycosylated antibody (FIG. 4).

Example 2: Conjugation of Trastuzumab with 3-APA Under Low-Ionic Strength Conditions Using Activa TI Microbial Transglutaminase The low-ionic strength conjugation method was also successfully demonstrated with Activa TI MTG enzyme purchased from Ajinomoto.

Conjugation of Trastuzumab under low-ionic strength conditions using buffer exchanged Activa TI microbial transglutaminase.

The Activa TI MTG is formulated with maltodextrin, a polysaccharide typically used as a food additive and for other applications. Initial conjugation experiments were conducted with resolubilized Activa TI MTG. Trastuzumab was exchanged into 10 mM potassium phosphate buffer pH 7.2 using a Zeba desalting column (Thermo), Activa TI powder was dissolved in 10 mM potassium phosphate buffer, and 3-APA was dissolved in water. Reaction components were combined in a reaction mixture with the final concentrations of Trastuzumab at 1 mg/mL, 3-APA at 690 uM, and Activa TI MTG at 20% w/v in 10 mM potassium phosphate pH 7.2. For comparison, an identical reaction was set up in PBS buffer (Trastuzumab 1 mg/mL, 3-APA 690 uM, Activa TI MTG 20% w/v, KH2PO4 1.5 mM, Na2HPO4 8.1 mM, KCl 2.7 mM, NaCl 137 mM pH 7). Reactions were incubated overnight at 37° C. For analysis, MTG was inactivated by the addition of MTG blocker and mAbs were deglycosylated with Rapid PNGase F (1% v/v) for 20 min at 50° C. and reduced with DTT to 50 mM followed by LC-MS to determine DOL.

The data showed that in the presence of maltodextrin, the DOL remains low and that the rate of conjugation was not increased despite modifying the buffer composition (Table 4).

Conjugation of Trastuzumab under low-ionic strength conditions using purified Activa TI microbial transglutaminase. To remove maltodextrin from the commercial MTG, the MTG obtained from Ajinomoto was purified from the Activa TI formulation by cation exchange chromatography (CEX) and further exchanged into low-salt buffer. 50 mg of Activa transglutaminase powder were dissolved in 500 ml of 20 mM sodium acetate pH 5.2. The sample was purified with a 5 ml SP HP HiTrap column (GE) attached to an Akta Avant at room temperature with a flow rate of 5 ml/min. The method includes a 5 column volume (CV) equilibration, 5 CV wash followed by a 0-55% gradient of buffer B over 20 CV (Buffer A=20 mM sodium acetate pH 5.2, Buffer B=20 mM sodium acetate pH 5.2, 1M NaCl). Fractions containing MTG were pooled and concentrated with an Amicon concentrator (MWCO=10 kDa). The concentrated enzyme was then exchanged into 10 mM phosphate buffer pH 7.2 with a Zeba desalting column.

Trastuzumab was incubated with the transglutaminase and 3-APA at the respective concentrations of 1 mg/ml antibody, 69 µM transglutaminase, and 690 µM 3-APA in 10 mM phosphate buffer pH 7.2 at 37° C. overnight. With this purified MTG, production of DOL=2 mAbs was increased by 4 fold under low-salt conditions compared to standard conditions (Table 4).

TABLE 4

Fraction of fully modified (to DOL = 2) Trastuzumab using buffer-exchanged or CEX-purified Activa TI MTG.

| Antibody | buffer | Enzyme | DOL of HC | % DOL 2 |
| --- | --- | --- | --- | --- |
| Trastuzumab | PBS | Buffer exchanged Activa TI | 0.45 | 20 |
| Trastuzumab | 10 mM potassium phosphate pH 7.2 | Buffer exchanged Activa TI | 0.44 | 19 |
| Trastuzumab | 10 mM potassium phosphate pH 7.2 | CEX-purified Activa TI | 0.9 | 81 |

DOL species were determined by LC-MS from reduced mass analysis of heavy chains (HC).

Example 3: Conjugation of PSMA Monoclonal Antibody

PSMB127, a human IgG4 mAb that binds to prostate-specific membrane antigen (PSMA), was conjugated with MTG under low-ionic strength conditions. PSMB127 was exchanged into 10 mM potassium phosphate buffer pH 7.2 using a Zeba desalting column (Thermo). Zedira MTG was exchanged into 10 mM potassium phosphate buffer, and 3-APA was dissolved in water. Components were combined in a reaction mixture with the final concentrations of PSMB127 at 1 mg/mL, 3-APA at 690 uM, and Zedira MTG at 10 U/mg in 0.9 mM potassium phosphate pH 7.2. For comparison, an identical reaction was set up in a PBS-based buffer (PSMB127 at 1 mg/mL, 3-APA at 690 uM, Zedira MTG at 10 U/mg in KH2PO4 1.5 mM, Na2HPO4 8.1 mM, KCl 2.7 mM, NaCl 167 mM, 5 mM sodium acetate pH 7). Reactions were incubated overnight at 37° C. For analysis, MTG was inactivated by the addition of MTG blocker and mAbs were deglycosylated with Rapid PNGase F (1% v/v) for 20 min at 50° C. and reduced with DTT to 50 mM or TCEP to 5 mM followed by LC-MS to determine DOL.

TABLE 5

Fraction of fully modified (to DOL = 2) intact WT human IgGs after 18-20 hours incubation with MTG and 3-APA at 37° C. in varying reaction conditions.

| Antibody | buffer | Enzyme | DOL of HC | % DOL 2 |
| --- | --- | --- | --- | --- |
| PSMB127† | PBS | Zedira | 0.73 | 53% |
| PSMB127† | 10 mM potassium phosphate pH 7.2 | Zedira | 1.00 | 100% |

DOL species were imputed from reduced mass analysis of heavy chains†.

Example 4: Conjugation of Pertuzumab with 3-APA Under Low-Ionic Strength Conditions Pertuzumab, a human IgG1 mAb that binds to Her2, was conjugated with MTG under low-ionic strength conditions. Clinical grade Pertuzumab was obtained from Genentech and was exchanged into 10 mM potassium phosphate buffer pH 7.2 using a Zeba desalting column (Thermo). Zedira MTG was exchanged into 10 mM potassium phosphate buffer, and 3-APA was dissolved in water. Components were combined in a reaction mixture with the final concentrations of Pertuzumab at 1 mg/mL, 3-APA at 690 uM, and Zedira MTG at 10 U/mg in 0.9 mM potassium phosphate pH 7.2. For comparison, an identical reaction was set up in a PBS-based buffer, with additional buffer components from the mAb and enzyme formulations (Pertuzumab 1 mg/mL, 3-APA 690 uM, and Zedira MTG 10 U/mg, in KH2PO4 1.5 mM, Na2HPO4 7.8 mM, KCl 2.6 mM, NaCl 163 mM, 5 mM sodium acetate, 0.6 mM histidine acetate, 3.9 mM sucrose, 0.001% polysorbate 20 pH 7). Reactions were incubated overnight at 37° C. For analysis, MTG was inactivated by the addition of MTG blocker and mAbs were deglycosylated with Rapid PNGase F (1% v/v) for 20 min at 50° C. and reduced with DTT to 50 mM or TCEP to 5 mM followed by LC-MS to determine DOL.

Reactions conducted in 10 mM potassium phosphate showed 100% conjugation while only 28% of Pertuzumab achieved a DOL of 2 in reactions conducted in PBS.

TABLE 6

Fraction of fully modified (to DOL = 2) intact WT human IgGs after 18-20 hours incubation with MTG and 3-APA at 37° C. in varying reaction conditions.

| Antibody | Buffer | DOL of HC | % DOL 2 |
| --- | --- | --- | --- |
| Pertuzumab† | PBS | 0.53 | 28% |
| Pertuzumab† | 10 mM potassium phosphate pH 7.2 | 1.00 | 100% |

DOL species were imputed from reduced mass analysis of heavy chains†.

Example 5: Conjugation of Panitumumab with 3-APA Under Low-Ionic Strength Conditions Panitumumab, a human IgG2 mAb that binds to EGFR, was conjugated with MTG under low-ionic strength conditions. Clinical grade Panitumumab was obtained from GSK and was exchanged into 10 mM potassium phosphate buffer pH 7.2 using a Zeba desalting column (Thermo). Zedira MTG was exchanged into 10 mM potassium phosphate buffer, and 3-APA was dissolved in water. Components were combined in a reaction mixture with the final concentrations of Panitumumab at 1 mg/mL, 3-APA at 690 uM, and Zedira MTG at 10 U/mg, in 0.9 mM potassium phosphate pH 7.2. For comparison, an identical reaction was set up in PBS-based buffer, with additional buffer components from the mAb and enzyme formulations (Panitumumab 1 mg/mL, 3-APA 690 uM, and Zedira MTG 10 U/mg in $KH_2PO_4$ 1.4 mM, $Na_2HPO_4$ 7.7 mM, KCl 2.6 mM, NaCl 165 mM, sodium acetate 8.6 mM, pH 7). Reactions were incubated overnight at 37° C. For analysis, MTG was inactivated by the addition of MTG blocker and mAbs were deglycosylated with Rapid PNGase F (1% v/v) for 20 min at 50° C. and reduced with DTT to 50 mM or TCEP to 5 mM followed by LC-MS to determine DOL.

Reactions conducted in 10 mM potassium phosphate showed 69% conjugation while only 28% of Panitumumab achieved a DOL of 2 in reactions conducted in PBS (Table 7).

TABLE 7

Fraction of fully modified (to DOL = 2) intact WT human IgGs after 18-20 hours incubation with MTG and 3-APA at 37° C. in varying reaction conditions.

| Antibody | buffer | DOL of HC | % DOL 2 |
| --- | --- | --- | --- |
| Panitumumab† | PBS | 0.53 | 28% |
| Panitumumab† | 10 mM potassium phosphate pH 7.2 | 0.83 | 69% |

DOL species were imputed from reduced mass analysis of heavy chains†.

Example 6: Conjugation of Trastuzumab to a Series of Substrates Under Low Ionic-Strength Conditions A series of amine-containing substrates were obtained for conjugation with MTG under low-salt conditions. 3 additional azide-containing amines of varying sizes were tested, with linkers between the amine and azide ranging in length from 11 to 71 atoms. The biotin-linked amine pentylamino-biotin was also tested, as was an amine linked to the cytotoxic payload MMAF. The substrates tested are shown in Table 8:

TABLE 8

Amine substrates tested in MTG-catalyzed conjugations. Substrates were dissolved in the indicated solvent at 50 mM.

| Substrate | Manufacturer | Catalog # | MW | solvent |
| --- | --- | --- | --- | --- |
| 3-Azidopropylamine | Click Chemistry Tools | AZ115 | 100 | water |
| Azido-PEG3-amine | Click Chemistry Tools | AZ101 | 218 | water |
| Azido-dPEG11-amine | Quanta Biodesign | 10524 | 570 | water |
| Azido-dPEG23-amine | Quanta Biodesign | 10525 | 1099 | water |
| Pentylamino biotin | ThermoFisher | 21345 | 328 | water |
| NH2-(xx)-PEG4-Val-Cit-PABC-MMAF | Levena Biopharma | custom | 1386 | DMSO |

To assess the conjugation efficiency under low ionic strength conditions, trastuzumab and Zedira MTG were exchanged into 5 mM potassium phosphate buffer pH 7.2 using Zeba desalting columns. Components were combined in a reaction mixture with the final concentrations of Trastuzumab at 1 mg/mL, substrate at 690 uM, and Zedira MTG at 10 U/mg, in 5 mM potassium phosphate pH 7.2. For comparison, an identical reaction was set up in PBS-based buffer, with additional buffer components from the mAb and enzyme formulations (Trastuzumab 1 mg/mL, substrate 690 uM, and Zedira MTG 10 U/mg in $KH_2PO_4$ 1.4 mM, $Na_2HPO_4$ 7.7 mM, KCl 2.6 mM, NaCl 165 mM, sodium acetate 8.6 mM, pH 7). Reactions were incubated at 37° C. for 18 hours. For analysis, MTG was inactivated by the addition of MTG blocker and mAbs were deglycosylated with Rapid PNGase F (1% v/v) for 20 min at 50° C. and reduced with DTT to 20 mM followed by LC-MS to determine DOL.

Reactions conducted in 5 mM potassium phosphate showed increased conjugation compared to the PBS reactions (Table 9). The series of azide-containing amines all showed increased conversion of the mAb to the DOL=2 species under the low-salt conditions. In general, the larger substrates gave less product than the smaller ones, both in PBS and 5 mM phosphate. The pentylamino biotin substrate was conjugated to 98% DOL=2 under low salt conditions and only 40% in PBS. The amine-vcMMAF molecule reached 50% conversion to DOL 2 under these conditions in 5 mM phosphate, and only 4% in PBS.

TABLE 9

Fraction of fully modified (to DOL = 2) trastuzumab after 18 hours incubation with MTG and amine substrate at 37° C. in 5 mM phosphate or PBS.

| | 5 mM phosphate | | PBS | |
| --- | --- | --- | --- | --- |
| Substrate | DOL of HC | % DOL 2 | DOL of HC | % DOL 2 |
| 3-Azidopropylamine† | 1 | 100% | 0.71 | 50% |
| Azido-PEG3-amine† | 1 | 100% | 0.68 | 46% |
| Azido-dPEG11-amine† | 0.91 | 83% | 0.51 | 26% |
| Azido-dPEG23-amine† | 0.86 | 74% | 0.51 | 26% |
| Pentylamino biotin† | 0.99 | 98% | 0.63 | 40% |
| NH2-PEG4-Val-Cit-PABC-MMAF† | 0.73 | 53% | 0.2 | 4% |

DOL species were imputed from reduced mass analysis of heavy chains†.

The various human IgGs antibodies of various isotypes and properties described above showed conjugation rate enhancement under low-ionic strength conditions. These included PSMB127, a human IgG4 mAb (Example 3), trastuzumab and pertuzumab, human IgG1 mAbs (Example 1, 2 and 4), and panitumumab, a human IgG2 mAb (example 5). Most showed >90% conjugation to DOL 2 under the inventive low-ionic strength conditions. In summary, reaction conditions have been identified in which WT human IgGs can be conjugated at Gln295 to full modification (DOL=2) in an MTG-catalyzed reaction, using a variety of amine substrates. No glycan engineering was necessary, and the glycan remained intact, preserving biophysical and immunological properties of the mAb.

These results demonstrate that the use of low-ionic strength buffer conditions provides consistent and reproducible labeling of glycan intact antibodies. At low-ionic strength conditions (e.g., at about 15 mM or less salt buffer, or about 12 mM or less salt buffer, or about 10 mM or less salt buffer, or about 10 mM salt buffer), 90% or more of the antibody consistently exhibits a DOL of 2 regardless of the nature of the antibody or the drug conjugate.

SEQUENCES

| SEQ ID NO | Description | Sequence |
|---|---|---|
| 1 | Trastuzumab light chain | DIQMTQSPSSLSASVGDRVTITCRASQDVNTAVA WYQQKPGKAPKLLIYSASFLYSGVPSRFSGSRSGT DFTLTISSLQPEDFATYYCQQHYTTPPTFGQGTKV EIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVT KSFNRGEC |
| 2 | Trastuzumab heavy chain | EVQLVESGGGLVQPGGSLRLSCAASGFNIKDTYIH WVRQAPGKGLEWVARIYPTNGYTRYADSVKGRFT ISADTSKNTAYLQMNSLRAEDTAVYYCSRWGGDG FYAMDYWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVDVSHEDPEVKFN WYVDGVEVHNAKTKPREEQYNSTYRVVSVLTVL HQDWLNGKEYKCKVSNKALPAPIEKTISKAKGQP REPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGK |
| 3 | PSMB127 light chain | EIVLTQSPATLSLSPGERATLSCRASQSVSSYLAW YQQKPGQAPRLLIYDASNRATGIPARFSGSGSGTD FTLTISSLEPEDFAVYYCQQRSNWPLTFGQGTKVE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKS FNRGEC |
| 4 | PSMB127 heavy chain | EVQLLESGGGLVQPGGSLRLSCAASGFTFKSDAMH WVRQAPGKGLEWVSEISGSGGYTNYADSVKGRFT ISRDNSKNTLYLQMNSLRAEDTAVYYCARDSYDSS LYVGDYFDYWGQGTLVTVSSASTKGPSVFPLAPCS RSTSESTAALGCLVKDYFPEPVTVSWNSGALTSGV HTFPAVLQSSGLYSLSSVVTVPSSSLGTKTYTCNVD HKPSNTKVDKRVESKYGPPCPPCPAPEAAGGPSVF LFPPKPKDTLMISRTPEVTCVVVDVSQEDPEVQFN WYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |

We claim:

1. A method of producing a conjugated antibody or a conjugated Fc fusion protein comprising reacting a glycosylated antibody or a glycosylated Fc fusion protein with an amine compound in the presence of transglutaminase in low-ionic strength condition, wherein:

the low-ionic strength condition is a buffer condition in which the salt concentration of the buffer solution is kept or brought to a concentration below about 30 mM;

the low-ionic strength condition is provided before said reacting takes place;

the glycosylated antibody comprises a heavy chain selected from the group consisting of an IgA1, IgA2, IgD, IgE, IgG1, IgG2, IgG3, IgG4, and IgM heavy chain;

the glycosylated Fc fusion protein comprises at least one Fc polypeptide linked to a protein or peptide by a C- or N-terminal fusion, wherein the Fc polypeptide of the Fc fusion protein comprises an IgG CH2 and an IgG CH3 constant domain sequence;

the glycosylated antibody or the glycosylated Fc fusion protein contains intact glycan content, and it contains N-linked glycans at amino acid Asn297, with numbering according to EU index described in Kabat;

the conjugated antibody or the conjugated Fc fusion protein is conjugated at its Fc domain;

the amine compound comprises a substrate selected from the group consisting of 3-azidopropylamine, azido-PEG3-amine, azido-dPEG11-amine, azido-dPEG23-amine, pentylamino biotin, and amino-PEG4-Val-Cit-PABC-MMAF; and the low-ionic strength condition is selected from the group consisting of
about 5 mM or about 10 mM phosphate buffer at pH 7.2,
about 2 mM to about 12 mM potassium phosphate at pH 5.8, 7.2, or 8.0,
about 2 mM to about 12 mM HEPES at pH 7.2 or 8.0,
about 2 mM to about 12 mM TRIS at pH 7.2, 8.0 or 9.2,
about 2 mM to about 12 mM sodium acetate at pH 5.6, and
about 2 mM to about 3 mM sodium acetate at pH 4.2.

2. The method of producing the conjugated antibody or the conjugated Fc fusion protein according to claim 1, wherein the glycosylated antibody or the glycosylated Fc fusion protein was not subject to treatment with endo or exo-glycosidase prior to reacting the glycosylated antibody or the glycosylated Fc fusion protein with the amine compound in the presence of the transglutaminase in the low-ionic strength condition.

3. The method of producing the conjugated antibody or the conjugated Fc fusion protein according to claim 1, wherein the glycosylation sites of the glycosylated antibody or the glycosylated Fc fusion protein were not glycan-engineered or glycan-modified prior to reacting the glycosylated antibody or the glycosylated Fc fusion protein with the amine compound in the presence of the transglutaminase in the low-ionic strength condition.

4. The method of producing the conjugated antibody or the conjugated Fc fusion protein according to claim 1 further comprises reducing the ionic strength of a solution containing the glycosylated antibody or the glycosylated Fc fusion protein to provide the low-ionic strength condition.

5. The method of producing the conjugated antibody or the conjugated Fc fusion protein according to claim 1, further comprising reducing the ionic strength of a solution containing the transglutaminase to provide the low-ionic strength condition.

6. The method of producing the conjugated antibody or the conjugated Fc fusion protein according to claim 4, wherein the ionic strength is reduced by dilution, buffer exchange through dialysis, diafiltration, filtration, precipitation and/or chromatographic methods.

7. The method of producing the conjugated antibody or the conjugated Fc fusion protein according to claim 1, wherein the transglutaminase is a microbial transglutaminase.

8. The method of producing the conjugated antibody or the conjugated Fc fusion protein according to claim 1, further comprising reacting the conjugated antibody with a reactive payload compound to form an antibody-payload conjugate.

9. The method of producing the conjugated antibody or the conjugated Fc fusion protein according to claim 1, further comprising determining the degree of labeling (DOL) by LC-MS.

10. The method of producing the conjugated antibody or the conjugated Fc fusion protein according to claim 1, wherein the conjugated antibody or the conjugated Fc fusion protein is conjugated at Gln295, with numbering according to EU index described in Kabat.

11. The method of producing the conjugated antibody or the conjugated Fc fusion protein according to claim 1, wherein the amine compound comprises a first click reaction partner, and the method further comprises reacting the conjugated antibody or the conjugated Fc fusion protein with a second click reaction partner that comprises one or more of a cytotoxic agent, cytostatic agent, chemotherapeutic agent, toxin, radionuclide, DNA, RNA, siRNA, microRNA, peptide nucleic acid, non-natural amino acid, peptide, enzyme, fluorescent tag, imaging agent, or biotin to obtain a second conjugate.

12. The method of producing the conjugated antibody or the conjugated Fc fusion protein according to claim 11, wherein the first click reaction partner is 3-azido-1-propylamine, and wherein the second click reaction partner is DBCO-val-cit-MMAF or DBCO-MMAF.

13. The method of producing the conjugated antibody or the conjugated Fc fusion protein according to claim 1, wherein reacting the glycosylated antibody with an amine compound comprises reacting the amine compound with 3-azido propylamine (3-APA), to form a (3-APA)-conjugated antibody.

14. The method of producing the conjugated antibody or the conjugated Fc fusion protein according to claim 13, wherein at least 80% of said glycosylated antibody or said glycosylated Fc fusion protein is converted to said conjugated antibody or said conjugated Fc fusion protein with an average degree of labeling (DOL) of two 3-APA per antibody at Gln295, numbering according to EU index as described in Kabat.

15. The method of producing the conjugated antibody or the conjugated Fc fusion protein according to claim 14, wherein 80% of said glycosylated antibody or said glycosylated Fc fusion protein is converted to said conjugated antibody or said conjugated Fc fusion protein.

16. The method of producing the conjugated antibody or the conjugated Fc fusion protein according to producing the conjugated antibody or the conjugated Fc fusion protein according to claim 14, wherein the 90% of said glycosylated antibody or said glycosylated Fc fusion protein is converted to said conjugated antibody or said conjugated Fc fusion protein.

17. The method of producing the conjugated antibody or the conjugated Fc fusion protein according to claim 13, further comprising reacting the 3-APA-conjugated antibody with DBCO-val-cit-MMAF or with DBCO-MMAF to form a DBCO-val-cit-MMAF-conjugated antibody or a DBCO-MMAF-conjugated antibody.

\* \* \* \* \*